(12) United States Patent
West et al.

(10) Patent No.: US 7,750,163 B2
(45) Date of Patent: Jul. 6, 2010

(54) CYANINE DYE LABELLING REAGENTS

(75) Inventors: Richard M. West, Cardiff (GB); Nigel Bosworth, Cardiff (GB); Ratnakar B. Mujumdar, Wexford, PA (US)

(73) Assignees: GE Healthcare U.K. Limited, Buckinghamshire (GB); Carnegie Mellon University, Pittsburgh, PA (US)

( * ) Notice: Subject to any disclaimer, the term of this patent is extended or adjusted under 35 U.S.C. 154(b) by 461 days.

(21) Appl. No.: 10/576,956

(22) PCT Filed: Oct. 29, 2004

(86) PCT No.: PCT/GB2004/004573

§ 371 (c)(1), (2), (4) Date: Nov. 27, 2006

(87) PCT Pub. No.: WO2005/044923

PCT Pub. Date: May 19, 2005

(65) Prior Publication Data

US 2007/0203343 A1    Aug. 30, 2007

Related U.S. Application Data

(60) Provisional application No. 60/516,428, filed on Oct. 31, 2003.

(51) Int. Cl.
*C07D 277/60* (2006.01)
(52) U.S. Cl. ...................................... 548/148
(58) Field of Classification Search ............... 548/148
See application file for complete search history.

(56) References Cited

U.S. PATENT DOCUMENTS

| 5,268,486 A | 12/1993 | Waggoner et al. |
| 6,974,873 B2 * | 12/2005 | Leung et al. ............... 548/455 |
| 2002/0077487 A1 | 6/2002 | Leung et al. |

FOREIGN PATENT DOCUMENTS

| JP | 04186342 | 7/1992 |
| JP | 0531330 | * 11/1993 |
| JP | 05313304 | 11/1993 |
| JP | 04186342 | * 7/1999 |
| WO | 02/26891 | 4/2002 |

OTHER PUBLICATIONS

PCT/GB2004/004573 Int'l Search Report and Written Opinion dated Apr. 2005.
PCT/GB2004/004573 Int'l Preliminary Examination Report dated Mar. 2006.

* cited by examiner

*Primary Examiner*—D. Margaret Seaman
*Assistant Examiner*—Nizal S Chandrakumar
(74) *Attorney, Agent, or Firm*—Craig Bohlken

(57) ABSTRACT

Disclosed are cyanine dyes that are useful for labeling and detecting biological and other materials. The dyes are of formula (I) in which groups $R^3$ and $R^4$ are attached to the $Z^1$ ring structure and groups $R^5$ and $R^6$ are attached to the $Z^2$ ring structure, and n=1, 2 or 3; $Z^1$ and $Z^2$ independently represent the carbon atoms necessary to complete a one ring, or two-fused ring aromatic system; at least one of groups $R^1$, $R^2$, $R^3$, $R^4$, $R^5$, $R^6$ and $R^7$ is the group -E-F where E is a single bond or a spacer group and F is a target bonding group; one or more of groups $R^{11}$, $R^{12}$, $R^{13}$ and $R^{14}$ are independently selected from the group —$(CH_2)_k$—W, where W is sulphonic acid or phosphonic acid and k is an integer from 1 to 10. The dyes may be used in fluorescence labeling applications, where the presence of one and preferably multiple water solubilising groups attached to the 3-position of the indolinium ring reduces dye-dye interactions, and hence dye-dye quenching, particularly where multiple dye molecules are attached to components such as nucleic acids, oligonucleotides, proteins and antibodies.

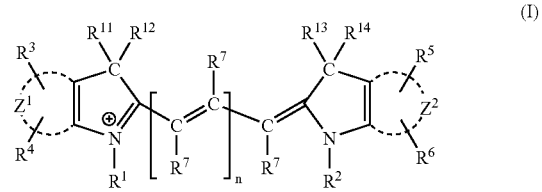

11 Claims, 9 Drawing Sheets

Plots of dye/protein ratio versus amount of applied NHS ester, for Compound 2 and Compound 6.

Absorption Spectra of IgG Conjugates of Compound 6 and Compound 2 at low- and high-dye/protein ratios.

Absorption Spectra of IgG Conjugates of Compound 7 compared with Compounds 3 and 4 at high-dye/protein ratios.

Plot of relative fluorescence intensity versus dye/protein ratio for heptamethine cyanine dyes.

Spectral scan (200-700nm) of cDNA labelled with Compound 2

Spectral scan (200-700nm) of cDNA labelled with Compound 5

Spectral scan (200-700nm) of cDNA labelled with Compound 6

CYANINE DYE LABELLING REAGENTS

This application is a filing under 35 U.S.C. 371 of international application number PCT/GB2004/004573, filed Oct. 29, 2004, which claims priority to application No. 60/516,428 filed Oct. 31, 2003, in the United States, the entire disclosure of which is hereby incorporated by reference.

The present invention relates to the field of labelling reagents, in particular reactive cyanine dyes having one or multiple water solubilising groups attached thereon and to methods utilising such dyes.

Fluorescent labels are established as the detection means of choice in microarray analysis. There are a number of different methods for producing nucleic acid probes labelled with fluorescent dyes. These include direct incorporation of dye-labelled nucleotides into cDNA using a reverse transcriptase enzyme system. One alternative is an indirect labelling approach and utilises a chemically reactive nucleotide analogue (e.g. aminoallyl-dUTP) or a biotinylated nucleotide analogue which is incorporated into a first strand cDNA during synthesis, followed by post-labelling with reactive or affinity dye labels, which bind either covalently or non-covalently to the modified nucleotide. Post-labelling strategies in microarray analyses have the potential to offer improved sensitivity of detection, especially for low expressed targets and enable the use of less mRNA. There is however, still a need for ultrasensitive detection methods such as may be obtained through the use of multiple labels, either through chemical labelling of the nucleic acid molecule, or through the use of avidin or streptavidin conjugates.

Cyanine dyes offer a number of advantages over other fluorescent dyes. The excitation and emission spectra of cyanine dyes span the visible and NIR spectrum from 450 nm to 800 nm. Furthermore, the cyanine dyes are characterised by having very high extinction coefficients, favourable quantum yields and good photostability. See for example, U.S. Pat. Nos. 6,048,982, 5,268,486, 5,569,587, (Waggoner, A. S. et al). Although post-labelling can result in a high level of incorporation of cyanine dye into the cDNA, or streptavidin, there is however, a tendency towards self-association of certain dyes in solution or at the solid-liquid interface, leading to a reduction of fluorescence quantum yields (Mishra, A. et al, Chem. Rev., (2000), 100(6), 1973-2012; Gruber, H. et al, Bioconjugate Chemistry, (2000), 11, 696-704).

WO 02/26891 (Molecular Probes Inc.) describes modified carbocyanine dyes and their conjugates with target materials, in which there is at least one substituted indolinium ring system, where the substitutent on the 3-position of the indolinium ring contains a chemically reactive group or a conjugated substance. The modified dyes according to WO 02/26891 are reported to overcome the tendency of cyanine dyes to self-associate (i.e. stack) and dye conjugates labelled with the modified dyes are reported to be more fluorescent than conjugates labelled with structurally similar carbocyanine dyes.

U.S. Pat. No. 6,083,485 (Licha et al) relates to an in-vivo diagnostic method based on near infra-red radiation (NIR) that uses dyes having the following structure:

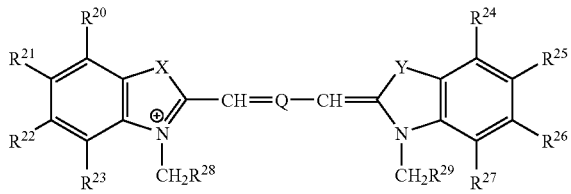

in which groups X and Y include the groups —$C(CH_2R^{32})(CH_2R^{33})$— and groups $R^{20}$ to $R^{29}$, $R^{32}$ and $R^{33}$ may be substituted with groups including hydroxy, carboxy, sulphonic acid, carboxyalkyl, alkoxycarbonyl or alkoxyoxoalkyl residues containing up to 10 carbon atoms, or a sulphoalkyl residue containing up to 4 carbon atoms.

Japanese Patent Application No. 5313304 (Fuji Photo Film Co. Ltd.) discloses a silver halide photographic sensitive material incorporating a dye containing multiple sulphonate groups and represented by the formula:

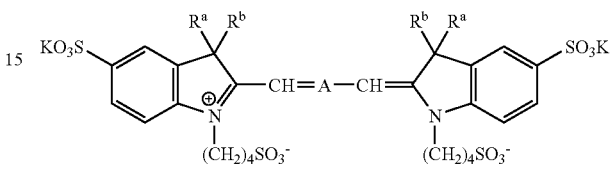

in which $R^a$ and $R^b$ may be alkyl carboxylate or alkyl sulphonate moieties.

None of the prior art documents specifically discloses a cyanine dye having one or more sulphonic acid or phosphonic acid water solubilising groups attached to the 3-position of the indolinium ring system, in which dye there is also provided at least one group suitable for direct covalent or non-covalent labelling of a target material. It has now been found that a new class of cyanine dye labelling reagents are useful for labelling and detecting biological and other materials. The presence of one, and preferably multiple, water solubilising groups attached to the 3-position of the indolinium ring has been found to reduce dye-dye interactions, particularly where multiple dye molecules are attached to components such as nucleic acids, proteins, antibodies, etc. As a result, the fall-off in fluorescence intensity, that is normally associated with multiply-labelled components and due to dye-dye stacking, is minimised.

Accordingly, in a first aspect there is provided a compound of formula (I):

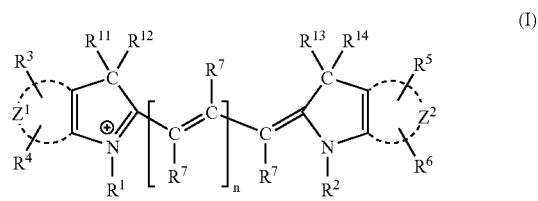

wherein:

groups $R^3$ and $R^4$ are attached to the $Z^1$ ring structure and groups $R^5$ and $R^6$ are attached to the $Z^2$ ring structure, and n=1, 2 or 3;

$Z^1$ and $Z^2$ independently represent the carbon atoms necessary to complete a one ring, or two-fused ring aromatic system;

at least one of groups $R^1$, $R^2$, $R^3$, $R^4$, $R^5$, $R^6$ and $R^7$ is the group -E-F where E is a single bond or a spacer group having a chain from 1-20 linked atoms selected from the group consisting of carbon, nitrogen and oxygen atoms and F is a target bonding group;

one or more of groups $R^{11}$, $R^{12}$, $R^{13}$ and $R^{14}$ are independently selected from the group —$(CH_2)_k$—W, where W is sulphonic acid or phosphonic acid and k is an integer from 1 to 10;

when any of groups $R^1$ and $R^2$ is not said group -E-F, said remaining groups $R^1$ and $R^2$ are independently selected from $C_1$-$C_6$ alkyl, benzyl either unsubstituted or substituted with sulphonic acid, and the group —$(CH_2)_k$—W, where W and k are hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen and sulphonic acid;

when any of groups $R^{11}$, $R^{12}$, $R^{13}$ and $R^{14}$ is not said group —$(CH_2)_k$—W, said remaining groups $R^{11}$, $R^{12}$, $R^{13}$ and $R^{14}$ are independently $C_1$-$C_6$ alkyl;

remaining groups $R^7$ are hydrogen or two of $R^7$ together with the group,

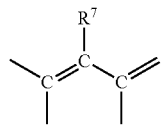

form a hydrocarbon ring system having 5 or 6 atoms.

Suitably, the compound according to the first aspect includes one or more counter-ions, which may be positive or negative to balance the formal charge (or charges) on the dye chromophore. The nature of the counter-ion is not material to the invention and could be one of many known ions such as $NH_4^+$, $K^+$, $Na^+$, trifluoroacetate ($F_3C$—$CO_2^-$), perchlorate ($ClO_4^-$), $Br^-$, or $I^-$. In the context of the present invention, it is to be understood that the terms "sulphonic acid" and "phosphonic acid" will also include respectively the groups "sulphonate" and "phosphonate", since they are the ionised forms of the parent acids.

Suitably, at least two of groups $R^{11}$, $R^{12}$, $R^{13}$ and $R^{14}$ are the group —$(CH_2)_k$—W. In a preferred embodiment, one of groups $R^{11}$ and $R^{12}$, and one of groups $R^{13}$ and $R^{14}$ is the group —$(CH_2)_k$—W, wherein W and k are hereinbefore defined. In these embodiments, remaining groups $R^{11}$ or $R^{12}$ and $R^{13}$ or $R^{14}$ are preferably methyl. In preferred embodiments, compounds of the present invention are those in which W is sulphonic acid. Preferably k is 3 or 4. Particularly preferred —$(CH_2)_k$—W is selected from —$(CH_2)_3$—$SO_3H$ and —$(CH_2)_4$—$SO_3H$.

Suitably, when any of groups $R^1$ and $R^2$ is not said group -E-F, said remaining groups $R^1$ and $R^2$ may be selected from $C_1$-$C_6$ alkyl, benzyl either unsubstituted or substituted with sulphonic acid, and the group —$(CH_2)_k$—W, where W and k are hereinbefore defined. Preferably, said remaining groups $R^1$ and $R^2$ may be selected from $C_1$-$C_6$ alkyl, sulphobenzyl and the group —$(CH_2)_k$—W. Preferred alkyl groups are methyl and ethyl.

In dyes according to the first aspect, when $R^7$ is substituted by group -E-F, it is preferably substituted in the meso-position, by which it is meant that the central $R^7$ group in the polymethine chain linking the heterocyclic ring structures may be substituted with a target bonding group. Any remaining $R^7$ groups that occur in the polymethine chain are hydrogen.

Suitably, $Z^1$ and $Z^2$ are independently selected from phenyl and naphthyl. Particular examples of cyanine dyes according to the compound of formula (I) and having one or two fused ring aromatic systems are shown as structures (II), (III), (IV), (V) and (VI) in Table 1.

TABLE 1

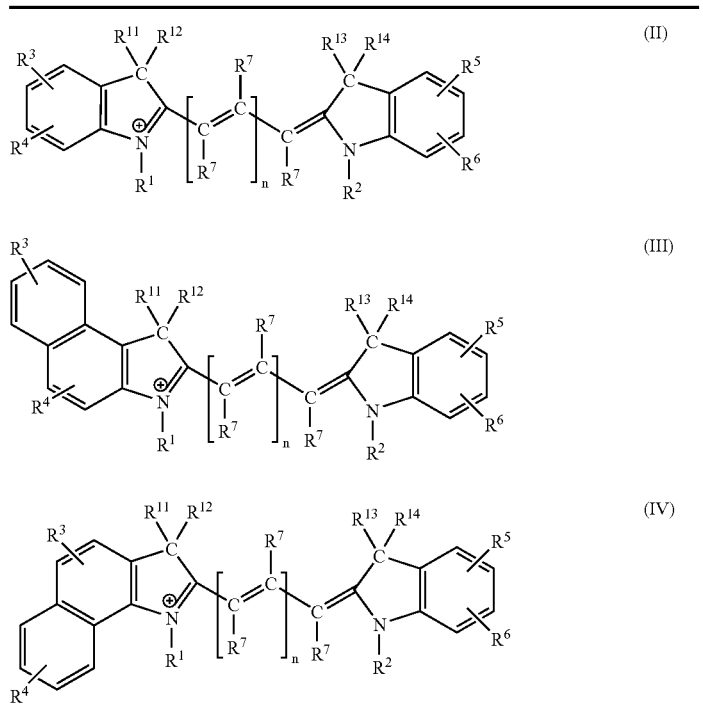

TABLE 1-continued

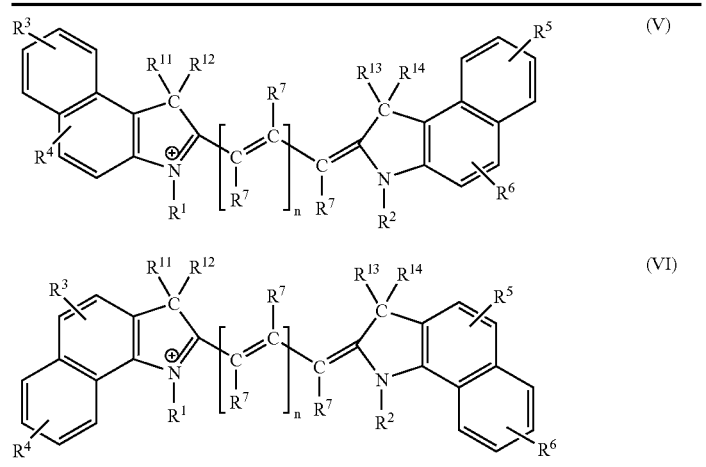

Examples of compounds in which groups $R^7$ form a hydrocarbon ring system are shown in Table 2 as structures (VII) and (VIII). In structures (II) to (VIII), groups $R^1$, $R^2$, $R^3$, $R^4$, $R^5$, $R^6$, $R^7$, $R^{11}$, $R^{12}$, $R^{13}$, $R^{14}$ and n are as hereinbefore defined.

TABLE 2

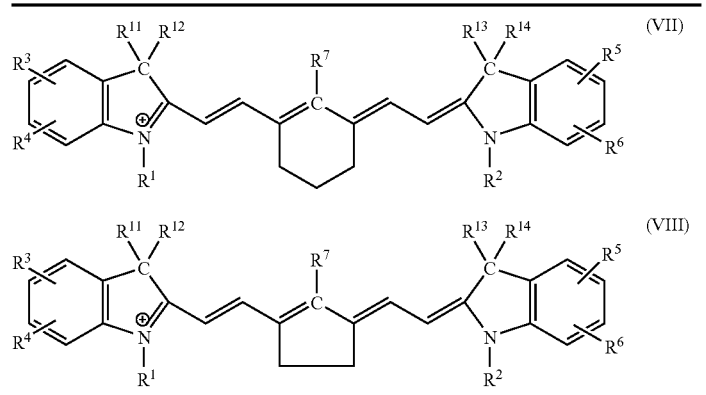

The linking moiety E links the target bonding group F with the chromophore moiety of the compounds according to formula (I). In one embodiment, the target bonding group F may be attached directly to the $R^3$, $R^4$, $R^5$, $R^6$ or $R^7$ positions of the dye, in which case E is a single covalent bond. In another, preferred embodiment, the target bonding group F may be covalently attached to the $R^1$, $R^2$, $R^3$, $R^4$, $R^5$, $R^6$ or $R^7$ positions of the dye indirectly, via a spacer group. In this embodiment, E is suitably a straight or branched chain of from 1 to 20 linked atoms containing carbon, nitrogen and oxygen atoms. Preferably, the spacer group E is selected from:

—(CHR')$_p$-Q-(CHR')$_r$— where Q is selected from: —CHR'—, —NR'—, —O—, —CR'=CR'—, —Ar—, —C(O)—NR'— and —C(O)—O—; R' is hydrogen or $C_1$-$C_4$ alkyl, p is 0-5 and r is 1-5.

Particularly preferred linkers are those wherein Q is selected from: —CHR'—, —C(O)—NH— and —⟨benzene-1,4-diyl⟩—;

where R' is hereinbefore defined.

The dyes according to the present invention contain at least one group -E-F, usually not more than two, and preferably one. In one embodiment, the target bonding group F is a group that reacts with a complementary group of a target component, with the formation of a covalent linkage between the dye and the component. In this embodiment, the choice of bonding group will depend on the groups that are available on the component to be labelled and, as such, will be well known to those skilled in the art. For example, the target bonding group may be a reactive group that can react under suitable conditions with a complementary functional group of a component. Examples of functional groups present in components, such as proteins, peptides, nucleic acids carbohydrates and the like, include hydroxy, amino, sulphydryl, carbonyl (including aldehyde and ketone) and thiophosphate. Alternatively, the target bonding group F may be a functional group and the target may contain, or be derivatised to contain a reactive constituent, such that the functional group of the dye may be reacted under suitable conditions with the reactive group of the target component. In either case, the component becomes labelled with the dye according to formula (I). Suitably, reactive groups F may be selected from carboxyl, succinimidyl ester, sulpho-succinimidyl ester, isothiocyanate, maleimide, haloacetamide, acid halide, hydrazide, vinylsulphone, dichlorotriazine and phosphoramidite. Preferably, the reactive group is a succinimidyl ester of a carboxylic acid, an isothiocyanate, a maleimide, a haloacetamide or a phosphoramidite. When F is a functional group, it is suitably selected from hydroxy, amino, sulphydryl, carbonyl (including aldehyde and ketone) and thiophosphate. By virtue of these reactive and functional groups the compounds of formula (I) may be reacted with and become covalently bound to the target component.

Examples of reactive groups $R^1$, $R^2$, $R^3$, $R^4$, $R^5$, $R^6$ and $R^7$ in the compound according to formula (I) and the groups with which groups $R^1$, $R^2$, $R^3$, $R^4$, $R^5$, $R^6$ and $R^7$ can react are provided in Table 3. In the alternative, $R^1$, $R^2$, $R^3$, $R^4$, $R^5$, $R^6$ and $R^7$ may be the functional groups of Table 3 which would react with the reactive groups of a target component.

TABLE 3

Possible Reactive Substituents and Functional Groups Reactive Therewith

| Reactive Groups | Functional Groups |
|---|---|
| succinimidyl ester, sulphosuccinimidyl ester | primary amino, secondary amino |
| anhydrides, acid halides | primary amino, secondary amino, hydroxyl |
| isothiocyanate | amino groups |
| vinylsulphone | amino groups |
| dichlorotriazines | amino groups |
| haloacetamides, maleimides | thiols, imidazoles, hydroxyl, amines, thiophosphates |
| carbodiimide | carboxylic acids |
| hydrazine, hydrazide | carbonyl including aldehyde and ketone |
| phosphoramidites | hydroxyl groups |

Particularly preferred reactive groups $R^1$, $R^2$, $R^3$, $R^4$, $R^5$, $R^6$ and $R^7$ which are especially useful for labelling target components with available amino and hydroxyl functional groups include:

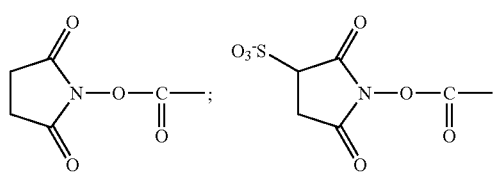

Particularly preferred reactive groups $R^1$, $R^2$, $R^3$, $R^4$, $R^5$, $R^6$ and $R^7$ which are useful for labelling target components with available thiol functional groups include:

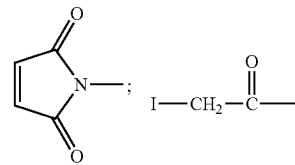

Particularly preferred examples of the group -E-F are those which comprise a carboxypentyl group E, for example:

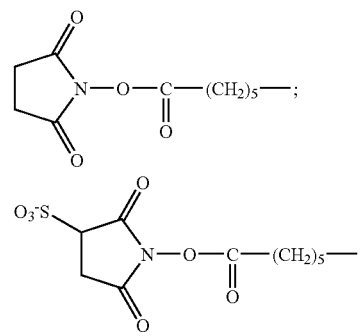

In another embodiment, the target bonding group F may be an affinity tag which is capable of binding specifically and non-covalently with its complementary specific binding partner. Examples of specific binding partner pairs include, but are not restricted to: biotin/avidin, biotin/streptavidin, polyhistidine tag-metal ion complexes with nitrilotriacetic acid (e.g. $Ni^{2+}$: NTA). The complementary specific binding partner may be one component of a labelling complex for detection of a target component. Thus, in one preferred labelling format, streptavidin, having four sites of attachment for a biotin label, may be used as a bridge linking a biotin group on the target component with a dye according to the present invention wherein group F is biotin, iminobiotin or desthiobiotin. It is to be understood that in the context of the present invention, any two atoms or molecules that possess a specific binding affinity, one for the other, may be employed. Preferred examples of affinity tags are selected from biotin, iminobiotin and desthiobiotin.

In further embodiments, the fluorescent cyanine dyes of the present invention may contain one or more additional sulphonic acid groups. In one embodiment, suitably, one or more sulphonic acid groups may be attached directly to the $Z^1$ and/or $Z^2$ ring structures. In an alternative embodiment, the $R^1$ and/or $R^2$ positions may be substituted directly with sulphobenzyl or the group —$(CH_2)_k$—W, where W and k are hereinbefore defined. In this embodiment, the dye may be optionally further substituted with one or more sulphonic acid groups attached directly to the $R^3$, $R^4$, $R^5$ and $R^6$ positions. Thus, the dyes according to the present invention may be substituted with up to five or more sulphonic acid groups, preferably between three and five sulphonic acid groups. The use of cyanine dyes substituted with three or more sulphonic acid groups for labelling biological target molecules results in a labelled product in which there is reduced dye-dye aggregation, negligible excited state interactions and therefore minimal dye-dye quenching and loss of fluorescence. The fluorescence emission intensity of a molecule so labelled with the preferred dyes of the present invention increases with the number of covalently attached dyes. Furthermore, substitution of the indolinium 3-position with sulphonic acid groups in addition to increasing the overall charge on the dye molecule, also adds steric bulk, thereby contributing to a reduction in dye-dye aggregation.

Halogen and halo groups are selected from fluorine, chlorine, bromine and iodine.

The following are more specific examples of cyanine dyes according to the invention, as shown in Table 4.

TABLE 4

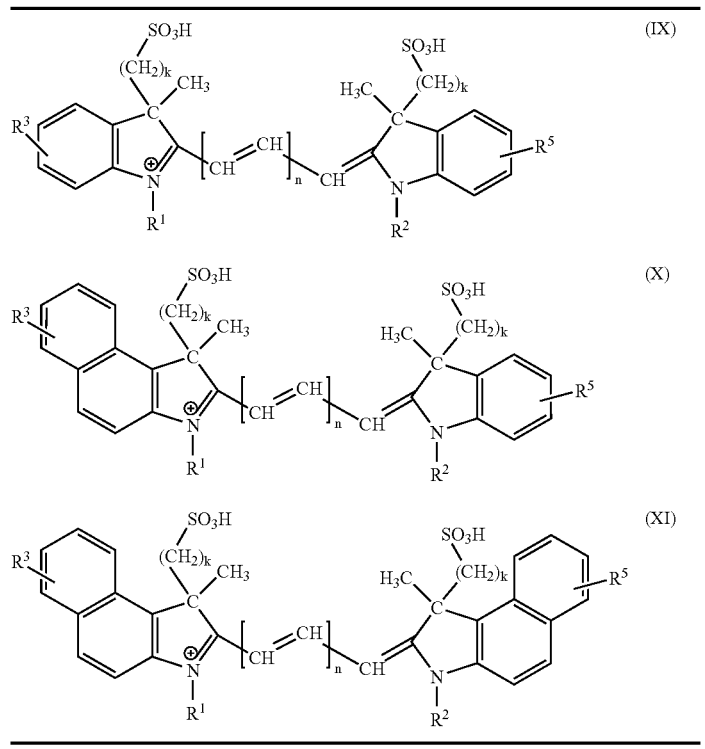

In structures (IX), (X) and (XI), n=1, 2 or 3;

at least one of groups $R^1$, $R^2$, $R^3$ and $R^5$ is the group -E-F where E and F are hereinbefore defined;

when any of groups $R^1$ and $R^2$ is not said group -E-F, said remaining groups $R^1$ and $R^2$ are independently selected from methyl, ethyl and —$(CH_2)_k$—W, where W is sulphonic acid and k is 3 or 4;

when any of groups $R^3$ and $R^5$ is not said group -E-F, said remaining groups $R^3$ and $R^5$ are independently selected from hydrogen and sulphonic acid, preferably sulphonic acid.

In structures (IX), (X) and (XI), group -E-F is suitably a succinimidyl ester derivative of an alkyl carboxylic acid, preferably 5-carboxypentyl, N-hydroxysuccinimidyl ester, or 5-carboxypentyl, N-hydroxy-sulphosuccinimidyl ester.

Particular examples of dyes according to the first aspect of the invention are as follows:

i) 2-{(1E,3E,5E)-5-[1-(5-carboxypentyl)-3-methyl-5-sulpho-3-(4-sulphobutyl-1,3-dihydro-2H-indol-2-ylidene]penta-1,3-dienyl}-1-ethyl-3-methyl-3-(4-sulphobutyl)-3H-indolium-5-sulphonate;

ii) 2-{(1E,3E,5E)-5-[1-(5-carboxypentyl)-3-methyl-5-sulpho-3-(4-sulphobutyl)-1,3-dihydro-2H-indol-2-ylidene]penta-1,3-dienyl}-3-methyl-1,3-bis(4-sulphobutyl)-3H-indolium-5-sulphonate;

iii) 2-{(1E,3E,5E,7E)-7-[1-(5-carboxypentyl)-3-methyl-5-sulpho-3-(4-sulphobutyl)-1,3-dihydro-2H-indol-2-ylidene]hepta-1,3,5-trienyl}-1-ethyl-3-methyl-3-(4-sulphobutyl)-3H-indolium-5-sulphonate;

iv) 2-{(1E,3E,5E,7E)-7-[5-(carboxymethyl)-3-methyl-1,3-bis(4-sulphobutyl)-1,3-dihydro-2H-indol-2-ylidene]hepta-1,3,5-trienyl}-1-ethyl-3-methyl-3-(4-sulphobutyl)-3H-indolium-5-sulphonate; and v) 1-benzyl-2-{1E,3E,5E-5-[1-(5-carboxypentyl)-3-methyl-5-sulpho-3-(4-sulphobutyl)-1,3-dihydro-2H-indol-2-ylidene]penta-1,3-dienyl}-3-methyl-3-(4-sulphobutyl)-3H-indolium-5-sulphonate.

The present invention also relates to labelling methods wherein the compounds of the present invention including at least group F attached to the $R^1$ to $R^7$ positions as hereinbefore defined may be used to label and thereby impart fluorescent properties to a target component. In particular, they may be used for multiple labelling and detection of biological molecules, such as nucleic acids, DNA, RNA, oligonucleotides, nucleotides, proteins, peptides, antibodies, etc. Thus, in a second aspect, there is provided a method for labelling a component, the method comprising:

i) contacting said component with a compound of formula (I):

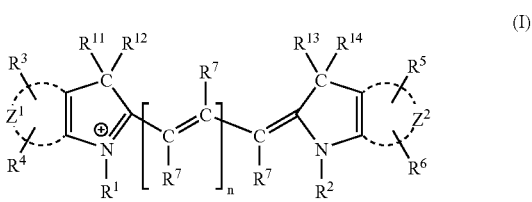

wherein:

groups $R^3$ and $R^4$ are attached to the $Z^1$ ring structure and groups $R^5$ and $R^6$ are attached to the $Z^2$ ring structure, and n=1, 2 or 3;

$Z^1$ and $Z^2$ independently represent the carbon atoms necessary to complete a one ring, or two-fused ring aromatic system;

at least one of groups $R^1$, $R^2$, $R^3$, $R^4$, $R^5$, $R^6$ and $R^7$ is the group -E-F where E is a single bond or a spacer group having a chain from 1-20 linked atoms selected from the group consisting of carbon, nitrogen and oxygen atoms and F is a target bonding group;

one or more of groups $R^{11}$, $R^{12}$, $R^{13}$ and $R^{14}$ are independently selected from the group —$(CH_2)_k$—W, where W is sulphonic acid or phosphonic acid and k is an integer from 1 to 10;

when any of groups $R^1$ and $R^2$ is not said group -E-F, said remaining groups $R^1$ and $R^2$ are independently selected from $C_1$-$C_6$ alkyl, benzyl either unsubstituted or substituted with sulphonic acid, and the group —$(CH_2)_k$—W, where W and k are hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen and sulphonic acid;

when any of groups $R^{11}$, $R^{12}$, $R^{13}$ and $R^{14}$ is not said group —$(CH_2)_k$—W, said remaining groups $R^{11}$, $R^{12}$, $R^{13}$ and $R^{14}$ are independently $C_1$-$C_6$ alkyl;

remaining groups $R^7$ are hydrogen or two of $R^7$ together with the group,

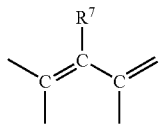

form a hydrocarbon ring system having 5 or 6 atoms; and ii) incubating said fluorescent dye with said component under conditions suitable for binding to and thereby labelling said component.

In one embodiment, the target bonding group F may be a group suitable for the formation of a covalent link between the compound of formula (I) and the target component, such as a reactive or functional group as hereinbefore defined. In the alternative, the target bonding group F is an affinity tag, for example biotin, desthiobiotin or iminobiotin, and the dye is bound to the target by non-covalent association. The method comprises incubating the component to be labelled with an amount of the compound according to the invention under conditions such that the dye becomes bound to the component. Methods for the formation of dye conjugates or complexes with target components will be well known to the skilled person. For example, covalent labelling of proteins is typically performed in an aqueous buffered medium, suitably bicarbonate at pH 9.0, at ambient temperature for a period of typically 1 hour. The reaction is normally carried out in the dark. The labelled protein can be separated from any unreacted dye by size exclusion chromatography, for example using Sephadex™ as the stationary phase and phosphate buffer, pH 7.0 as the eluant. For multiple labelling of a target biomolecule, the ratio of the amount or concentration of dye to target material should be adjusted accordingly. Suitable target biological components include, but are not limited to the group consisting of antibody, lipid, protein, peptide, carbohydrate, nucleotides which contain or are derivatized to contain one or more of an amino, sulphydryl, carbonyl, hydroxyl and carboxyl and thiophosphate groups, and oxy or deoxy polynucleic acids which contain or are derivatized to contain one or more of an amino, sulphydryl, carbonyl, hydroxyl, carboxyl and thiophosphate groups, microbial materials, drugs, hormones, cells, cell membranes and toxins.

In addition to the foregoing one-step labelling process, the present invention also relates to two-step labelling processes in which, in a first step, a dye according to the present invention binds to, and thereby labels a primary component, such as an antibody, protein, DNA probe, etc. In the second step of the labelling process, the fluorescently labelled primary component is then used as a probe for detection of a secondary component, such as an antigen for which the antibody is specific.

The compounds of the present invention can also be used to determine the concentration of a particular protein or other component in a system. If the number of reactive groups on a protein which can react with a probe is known, the fluorescence per molecule can be known and the concentration of these molecules in the system can be determined by the total fluorescence intensity of the system. This particular method can be used to measure the concentration of various labelled analytes using microtitre plate readers or other known immunofluorescence detection systems. The concentration of fluorescently labelled material can also be determined using, for example, fluorescence polarization detection instruments.

The compounds of the present invention may also be used in a detection method wherein a plurality of the fluorescent dyes are covalently attached to a plurality of different primary components, such as antibodies, each primary component being specific for a different secondary component, such as an antigen, in order to identify each of a plurality of secondary components in a mixture of secondary components. According to this method of use, each of the primary components is separately labelled with a fluorescent dye having a different light absorption and emission wavelength characteristic, compared with the dye molecules used for labelling the other primary components. The labelled primary components are then added to the preparation containing secondary components, such as antigens, and the primary components are allowed to attach to the respective secondary components for which they are selective.

Any unreacted probe materials may be removed from the preparation by, for example, washing, to prevent interference with the analysis. The preparation is then subjected to a range of excitation wavelengths including the absorption wavelengths of particular fluorescent compounds. A fluorescence microscope or other fluorescence detection system, such as a flow cytometer or fluorescence spectrophotometer, having filters or monochromators to select the rays of the excitation wavelength and to select the wavelengths of fluorescence is next employed to determine the intensity of the emission wavelengths corresponding to the fluorescent compounds utilized, the intensity of fluorescence indicating the quantity of the secondary component which has been bound with a particular labelled primary component. Known techniques for conducting multi-parameter fluorescence studies include, for example, multiparameter flow cytometry. In certain cases a single wavelength of excitation can be used to excite fluorescence from two or more materials in a mixture where each fluoresces at a different wavelength and the quantity of each labelled species can be measured by detecting its individual fluorescence intensity at its respective emission wavelength. If desired, a light absorption method can also be employed.

The detection method of the present invention can be applied to any system in which the creation of a fluorescent primary component is possible. For example, an appropriately reactive fluorescent compound can be conjugated to a DNA or RNA fragment and the resultant conjugate then caused to bind to a complementary target strand of DNA or RNA. Appropriate fluorescence detection equipment can then be employed to detect the presence of bound fluorescent conjugates.

The present invention relates to intermediates and to methods useful for preparing the dyes of formula (I) which are suitably prepared by a process comprising:

a) reacting a first intermediate compound having the formula (A):

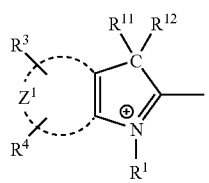

(A)

wherein $Z^1$, $R^1$, $R^3$, $R^4$, $R^{11}$ and $R^{12}$ are hereinbefore defined;

b) a second intermediate compound which may be the same or different from the first intermediate compound and having the formula (B):

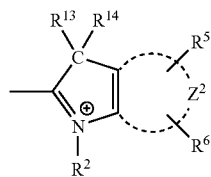

(B)

where $Z^2$, $R^2$, $R^5$, $R^6$, $R^{13}$ and $R^{14}$ are hereinbefore defined, and c) a third compound (C) suitable for forming a linkage between the first and second compounds;

provided that at least one of the groups $R^1$, $R^2$, $R^3$, $R^4$, $R^5$ and $R^6$ is the group -E-F, where E and F are hereinbefore defined; and provided that one or more of groups $R^{11}$, $R^{12}$, $R^{13}$ and $R^{14}$ are independently selected from the group —$(CH_2)_k$—W, where W is selected from sulphonic acid and phosphonic acid groups and k is an integer from 1 to 10.

Preferably, —$(CH_2)_k$—W is selected from —$(CH_2)_3$—$SO_3H$ and —$(CH_2)_4$—$SO_3H$.

According to the method, intermediate compounds (A), (C) and (B) may be reacted either in a single step or in a multiple step process to form the compounds of formula (I). Symmetrical compounds of formula (I) wherein structures (A) and (B) are the same may be suitably prepared by reacting a compound of formula (A) (or (B)) in two molar proportions with an appropriate bis-functional methine fragment containing 1, 3 or 5 carbon atoms, substituted with a group to form $R^7$ as hereinbefore defined. For example, a substituted N,N'-diphenylformamidine, or ortho ester will be employed as the third compound (C) for preparing trimethine cyanine dye analogues. In a corresponding manner, a suitably substituted malondialdehyde dianil may be employed for preparing the pentamethine cyanine dye analogues and a glutaconic aldehyde for preparing heptamethine cyanine dye analogues. The reaction is usually carried out in an organic solvent, such as pyridine and heated to reflux. The mixture subsequently is cooled and poured into an organic solvent such as ether. The resulting solid or semi-solid may be purified by chromatography on a silica gel column using a series of methanol/chloroform solvents.

Unsymmetrical compounds of formula (I) wherein structures (A) and (B) are different may be conveniently prepared in a two step process. In this process, an intermediate compound is first formed by reacting an indolinium compound of formula (A) with a compound suitable for forming the linkage, for example, a suitably substituted N,N'-diphenylformamidine, or malonaldehyde dianil, in the presence of acetic anhydride, to form a 2-anilinovinyl or 4-anilino-1,3-butadienyl quaternary salt. The intermediate quaternary salt may be reacted with a second 2-methyl indolinium quaternary salt to give a compound of formula (I). Alternative intermediates for forming the polymethine linkage joining the heterocyclic ring systems are known and are described for example in Hamer, F. M., "The Cyanine Dyes and Related Compounds", Interscience (1964).

It will be readily appreciated that certain dyes of the present invention may be useful as intermediates for conversion to other dyes by methods well known to those skilled in the art. The dyes of the present invention may be synthesized by the methods disclosed herein. Derivatives of the compounds having a particular utility are prepared either by selecting appropriate precursors or by modifying the resultant compounds by known methods to include functional groups at a variety of positions. Groups $R^1$, $R^2$, $R^3$, $R^4$, $R^5$, $R^6$ and $R^7$ may be chosen so that the dyes of the present invention have different wavelength characteristics, thereby providing a number of related dyes which can be used in multiparameter analyses wherein the presence and quantity of different compounds in a single sample may be differentiated based on the wavelengths of a number of detected fluorescence emissions.

Cy™ is a trademark of Amersham Biosciences UK Limited.

The invention is further illustrated by reference to the following examples and figures, in which.

Figure 1A:
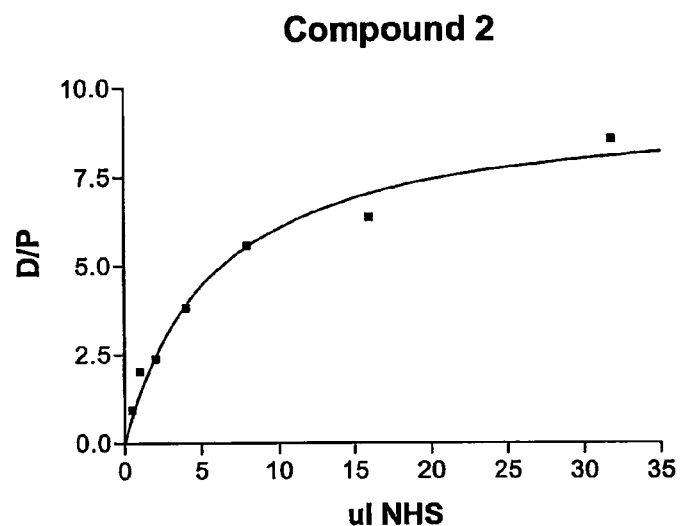
FIGS. 1 (A and B) are plots showing dye/protein ratio versus amount of applied NHS ester for Compound 2 and Compound 5.

EXAMPLES 1. 2-{(1E,3E,5E)-5-[1-(5-Carboxypentyl)-3-methyl-5-sulpho-3-(4-sulphobutyl)-1,3-dihydro-2H-indol-2-ylidene]penta-1,3-dienyl}-1-ethyl-3-methyl-3-(4-sulphobutyl)-3H-indolium-5-sulphonate (Compound 1)

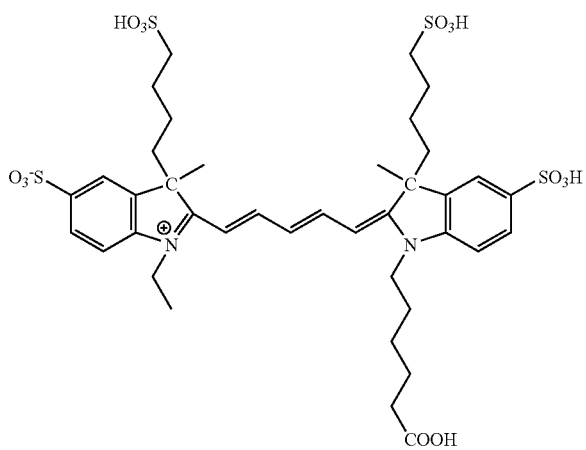

1.1 Sodium 5-(ethoxycarbonyl)-5-methyl-6-oxoheptane-1-sulphonate

Sodium hydride (60 wt %, 12 g=0.3 mol NaH) was slurried in dry DMF (100 ml). The resulting suspension was cooled with stirring to 0° C. To this was added a solution of ethyl 2-methylacetoacetate (50 g, 0.346 mol) in DMF (25 ml), dropwise so as to maintain the temperature at <10° C. and control effervescence. Once addition was complete and hydrogen evolution ceased, the mixture was warmed in a warm water bath until a clear, pale yellow solution resulted. This was cooled again to 0° C. A solution of 1,4-butanesultone (45 g, 0.33 mol) in DMF (25 ml) was added over 15 mins, maintaining the temperature at <10° C. Once addition was complete, the mixture was heated at 50° C. for 16 hrs. The solvent was then evaporated under vacuum to dryness; the residue was partitioned between water and diethyl ether. The aqueous layer was retained; the organic layer was extracted with fresh water, then discarded. The combined aqueous extracts were washed with fresh ether, then evaporated under vacuum to give the product as a waxy solid.

$^{1}$H-nmr (D$_2$O) δ 4.23 (2H, q), 2.9 (2H, app t), 2.26 (3H, s), 2.0-1.6 (6H, m), 1.36 (3H, s) and 1.26 (3H, t).

1.2 5-Methyl-6-oxoheptane-1-sulphonic acid

The above material was heated at 90° C. in concentrated hydrochloric acid (200 ml), until TLC indicated complete reaction (~3 hrs). The solvent was then evaporated under vacuum; the residue was purified by flash chromatography (Silica. Ethanol/dichloromethane mixtures) to give 49.6 g of 5-methyl-6-oxoheptane-1-sulphonic acid.

$^{1}$H-nmr (D$_2$O) δ 2.9 (2H, app t), 2.68 (1H, m), 2.2 (3H, s), 1.8-1.3 (6H, m) and 1.18 (3H, d).

1.3 2,3-Dimethyl-3-(4-sulphobutyl)-3H-indole-5-sulphonic acid

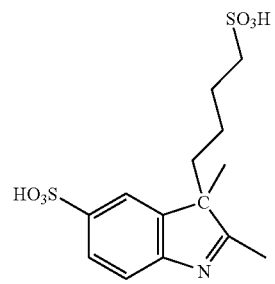

4-Hydrazinobenzenesulphonic acid (7.5 g), 5-methyl-6-oxoheptane-1-sulphonic acid (11.0 g) and acetic acid (50 ml) were heated under reflux under nitrogen for 6 hrs, during which time all of the suspended solid dissolved. The solvent was then evaporated under vacuum and the residue triturated with 2-propanol at 80° C. to give a light brown solid in suspension. The mixture was allowed to cool to ambient temperature, the solid collected by filtration, washed with 2-propanol and diethyl ether and dried under vacuum. The product was purified by HPLC, collecting the major peak detected at 270 nm. (Phenomenex Jupiter 15μ C18 300A, 250×50 mm. 100 ml/min. 0.5 g per run. Eluant isocratic water+0.1% TFA). Product fractions were pooled and evaporated to give 11.1 g.

UV/Vis is (Water+0.1% TFA): 269, 229 nm $^{1}$H-nmr (D$_2$O) δ 0.9 (2H, m), 1.6 (3H, s+2H, m), 2.15 (2H, m), 2.75 (2H, m), 2.8 (CH$_3$ singlet mostly exchanged), 7.8 (1H, d), 8.0 (1H, dd) and 8.1 (1H, d).

LC-MS: found 362. MH$^+$=C$_{14}$H$_{20}$NO$_6$S$_2$ requires 362.

1.4 Disodium 2,3-dimethyl-3-(4-sulphonatobutyl)-3H-indole-5-sulphonate

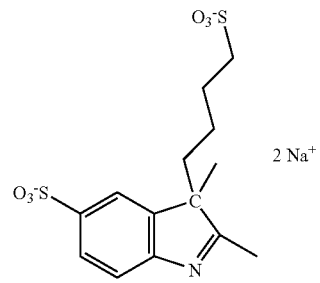

2,3-dimethyl-3-(4-sulphobutyl)-3H-indole-5-sulphonic acid (3.6 g. 9.8 mmol) was dissolved in water (50 ml). The resulting solution was neutralized with sodium acetate to a pH of ~7, then the solvent was evaporated under vacuum. The sticky residue was co-evaporated with methanol, then triturated with ether to give a fine solid. This was dried under high vacuum over phosphorus pentoxide to give the title disodium salt which was used directly without purification.

$^{1}$H-nmr (D$_2$O) δ 0.6-0.8 (2H, m), 1.4 (3H, s), 1.6 (2H, m), 1.9-2.15 (2H, broad m+s for acetate) 2.35 (CH$_3$ singlet mostly exchanged), 2.75 (2H, app t), 7.6 (1H, d) and 7.83 (2H, m).

1.5 1-Ethyl-2,3-dimethyl-3-(4-sulphobutyl)-3H-indolium-5-sulphonate salt

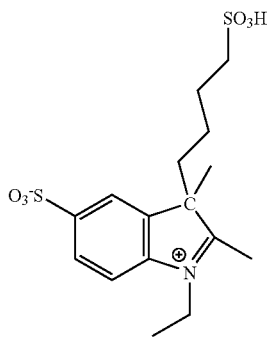

Disodium 2,3-dimethyl-3-(4-sulphonatobutyl)-3H-indole-5-sulphonate (1 g), ethyl-p-toluene sulphonate (0.95 ml; 5.56 mmol) and tetramethylenesulphone (10 ml) were heated together at 140° C. for 12 hrs. TLC (silica; 2:1 MeOH/EtOAc) showed the formation of a new product spot (rf=0.8), which turned magenta on standing. The product was precipitated into ethyl acetate and then filtered off and dried in vacuo to give the crude product as a dark purple solid; 1.5 g. The product was purified in multiple shots by HPLC (Vydac protein & peptide C18 (250 mm×25 mm); flow rate 10 ml/min; gradient of 0 to 25% B over 30 mins; eluant A=0.1% TFA in water and eluant B=0.1% TFA in acetonitrile; detection at 220 nm). The fractions containing the desired product were pooled and the solvent removed under reduced pressure. The product was obtained as a pale pink oil (400 mg).

LC-MS (ES+): found 390. MH$^+$=C$_{16}$H$_{24}$NO$_6$S$_2$) requires 390.

$^1$H NMR (D$_2$O) δ 0.86 (m, 2H), 1.56 (t, 3H), 1.75 (2xs, 5H), 2.36(m, 2H), 2.75 (m, 2H), 4.60 (q, 2H), 7.96, 8.10 (dd, 2H), 8.15 (s, 1H).

1.6 1-(5-Carboxypentyl)-2,3-dimethyl-3-(4-sulphobutyl)-3H-indolium-5-sulphonate

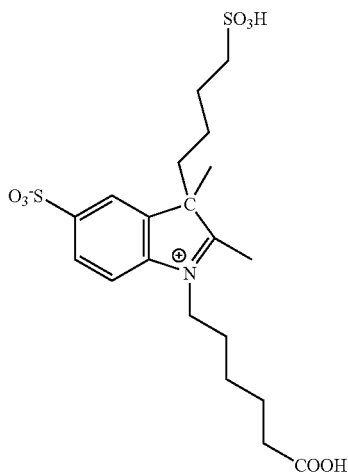

Disodium 2,3-dimethyl-3-(4-sulphonatobutyl)-3H-indole-5-sulphonate (1 g), 6-bromohexanoic acid (3.2 g, 16.41 mmol) and tetramethylene sulphone (5 ml) were heated together at 110° C. under nitrogen for 14 hrs. A further aliquot (3.2 g, 16.41 mmol) of bromohexanoic acid was then added and heating continued for 12 hrs. A further aliquot (1.6 g, 8.21 mmol) of 6-bromohexanoic acid was then added and heating continued for a further 12 hrs. The reaction mixture was cooled to RT and then poured into ethyl acetate. The product was filtered off, washed with ethyl acetate and then dried in vacuo at 40° C. and obtained as a brown solid (2.71 g). The product was purified as required by HPLC (Vydac protein & peptide C18 (250 mm×25 mm); flow rate 10 ml/min; gradient of 0 to 25% B over 30 mins; eluant A=0.1% triethylamine in water and eluant B=0.1% triethylamine in methanol; detection at 220 nm). Fractions containing the desired product were pooled and the solvent removed under reduced pressure. The product was obtained as yellowish brown oil, from crude material (100 mg) the purified product was obtained as the triethyl ammonium salt (56 mg).

LC-MS (ES+): found 476. MH$^+$=C$_{20}$H$_{30}$NO$_8$S$_2$ requires 476.

$^1$H NMR (D$_2$O) δ 0.85 (m, 2H), 1.3 (t, 27H), 1.50 (m, 2H), 1.62(m, 9H), 2.00 (m, 2H), 2.25 (m, 4H), 2.39 (m, 1H), 2.75 (m, 2H), 3.20 (q, 18H), 4.55 (t, 2H), 7.95, 8.10 (dd, 2H), 8.14 (s, 1H).

1.7 2-[(1E,3E)-4-Anilinobuta-1,3-dienyl]-1-ethyl-3-methyl-3-(4-sulphobutyl)-3H-indolium-5-sulphonate

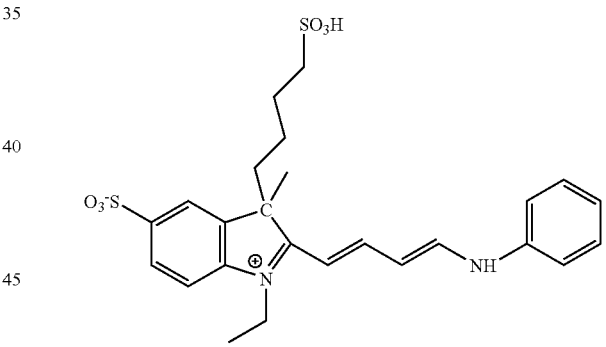

1-Ethyl-2,3-dimethyl-3-(4-sulphobutyl)-3H-indolium-5-sulphonate, crude (1.1 g), malonaldehyde bis(phenylimine) HCl (0.5 g) and acetic acid (20 ml) were heated under nitrogen at 130° C. for 8 hrs to give a dark orange-red solution. The solvent was then evaporated under vacuum; the residue was partitioned in a water/dichloromethane/methanol mixture. UV/Vis is analysis (ethanol) confirmed the presence of the product in the upper, aqueous layer (λ$_{max}$=524 nm) while the malonaldehyde starting material was present only in the lower, organic layer (λ$_{max}$=384 nm). The aqueous layer was evaporated under vacuum and purified by HPLC (water/0.1% TFA and acetonitrile/0.1% TFA eluants). Fractions containing the product were pooled and evaporated, with final drying under high vacuum over phosphorus pentoxide to give the title product.

UV/Vis is (Water+0.1% TFA): 520 nm.

MS (MALDI-TOF): M+518.

1.8 2-{(1E,3E,5E)-5-[1-(5-Carboxypentyl)-3-methyl-5-sulpho-3-(4-sulphobutyl)-1,3-dihydro-2H-indol-2-ylidene]penta-1,3-dienyl}-1-ethyl-3-methyl-3-(4-sulphobutyl)-3H-indolium-5-sulphonate 2-[(1E,3E)-4-Anilinobuta-1,3-dienyl]-1-ethyl-3-methyl-3-(4-sulphobutyl) 3H-indolium-5-sulphonate (71 mg) was dissolved in a mixture of pyridine (45): acetic acid (45): acetic anhydride (10) (5 ml), at 90° C. To this solution was added crude 1-(5-carboxypentyl)-2,3-dimethyl-3-(4-sulphobutyl)-3H-indolium-5-sulphonate, portionwise at 20 minute intervals, until UV/Vis is analysis indicated complete conversion of half-dye components ($\lambda_{max}$=524, 430 nm) to Cy5 dye product ($\lambda_{max}$=653 nm). The solvent was then evaporated under vacuum and the residue purified by HPLC (RPC18. Water/methanol/triethylamine, then water/acetonitrile/TFA).

UV/Vis is (Water+0.1% TFA): 653 nm.

MS (MALDI-TOF): found 902. $MH^+$=$C_{39}H_{53}N_2O_{14}S_4$ requires 901.

2. 2-{(1E,3E,5E)-5-[1-(5-Carboxypentyl)-3-methyl-5-sulpho-3-(4-sulphobutyl)-1,3-dihydro-2H-indol-2-ylidene]penta-1,3-dienyl}-3-methyl-1,3-bis(4-sulphobutyl)-3H-indolium-5-sulphonate (Compound 2)

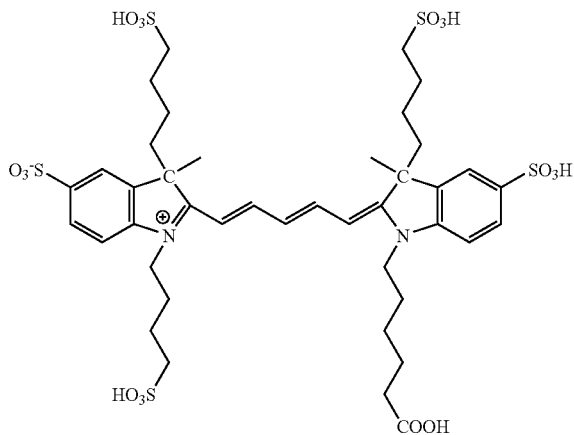

2.1 Disodium 2,3-dimethyl-1,3-bis(4-sulphonatobutyl)-3H-indolium-5-sulphonate

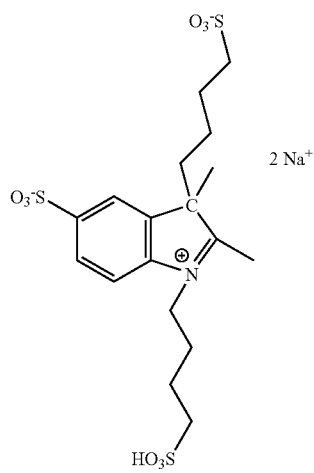

Disodium 2,3-dimethyl-3-(4-sulphonatobutyl)-3H-indole-5-sulphonate (1.0 g) and 1,4-butanesultone (10 ml) were mixed and heated under nitrogen at 150° C. for 52 hrs to give a dark purple slurry. After cooling, the mixture was triturated with ethyl acetate: the solid portion was collected by filtration, washed with ethyl acetate and diethyl ether, then dried under high vacuum over phosphorus pentoxide to give the title product (1.45 g), which was used directly without purification.

2.2 2-[(1E,3E-4-Anilinobuta-1,3-dienyl]-3-methyl-1,3-bis(4-sulphobutyl)-3H-indolium-5-sulphonate

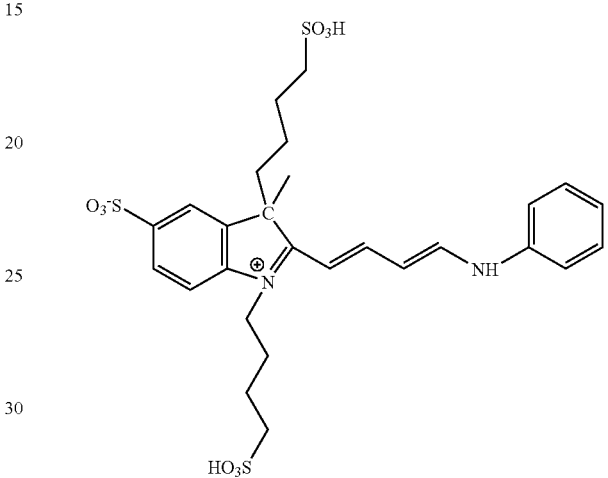

Disodium 2,3-dimethyl-1,3-bis(4-sulphonatobutyl)-3H-indolium-5-sulphonate, crude (1.0 g) and malonaldehyde bis (phenylimine) HCl (1.0 g) and acetic acid (10 ml) were heated under nitrogen at 130° C. for 10 hrs to give a dark orange-red solution. The solvent was then evaporated under vacuum; the residue was partitioned in a water/dichloromethane/methanol mixture. UV/Vis is analysis (ethanol) confirmed the presence of the product in the upper, aqueous layer ($\lambda_{max}$=524 nm) while the malonaldehyde starting material was present mainly in the lower, organic layer ($\lambda_{max}$=384 nm). The aqueous layer was evaporated under vacuum and purified by HPLC (water/0.1% TFA and acetonitrile/0.1% TFA eluants). Fractions containing the product were pooled and evaporated, freeze-dried from aqueous solution, with final drying under high vacuum over phosphorus pentoxide to give the title product. Yield 240 mg as a red foam.

UV/Vis is (Water+0.1% TFA): 520 nm.

MS (MALDI-TOF): found 627. $MH^+$=$C_{27}H_{35}N_2O_9S_3$ requires 627.

$^1$H-nmr ($D_2O$) δ 0.65 (1H, broad m), 0.95 (1H, broad m), 1.6 (2H, m), 1.7 (3H, s), 1.9 (4H, m), 2.3 (2H, m), 2.7 (2H, app t), 3.0 (2H, t), 4.1 (2H, app t), 6.4 (2H, m), 7.2-7.6 (6H, m), 7.8-8.0 (2H, m), 8.15 (1H, t) and 8.2 (1H, d).

2.3 2-{(1E,3E,5E)-5-[1-(5-carboxypentyl)-3-methyl-5-sulpho-3-(4-sulphobutyl)-1,3-dihydro-2H-indol-2-ylidene]penta-1,3-dienyl}-3-methyl-1,3-bis(4-sulphobutyl)-3H-indolium-5-sulphonate 2-[(1E,3E)-4-Anilinobuta-1,3-dienyl]-3-methyl-1,3-bis (4-sulphobutyl)-3H-indolium-5-sulphonate (70 mg) was dissolved in a mixture of pyridine (45): acetic acid (45): acetic anhydride (10) (5 ml), at 90° C. To this solution was added crude 1-(5-carboxypentyl)-2,3-dimethyl-3-(4-sulphobutyl)-3H-indolium-5-sulphonate, portionwise at 20 minute intervals, until UV/Vis is analysis indicated complete conversion of half-dye components ($\lambda_{max}$=524, 430 nm) to Cy5 dye product ($\lambda_{max}$=656 nm). The solvent was then evaporated under vacuum and the residue purified by HPLC (RPC18. Water/acetonitrile/TFA).

UV/Vis is (Water+0.1% TFA): 656 nm.

MS (MALDI-TOF): found 1010. $MH^+=C_{41}H_{57}N_2O_{17}S_5$ requires 1009.

3. 2-{(1E,3E,5E,7E)-7-[1-(5-Carboxypentyl)-3-methyl-5-sulpho-3-(4-sulphobutyl)-1,3-dihydro-2H-indol-2-ylidene]hepta-1,3,5-trienyl}-1-ethyl-3-methyl-3-(4-sulphobutyl)-3H-indolium-5-sulphonate (Compound 3)

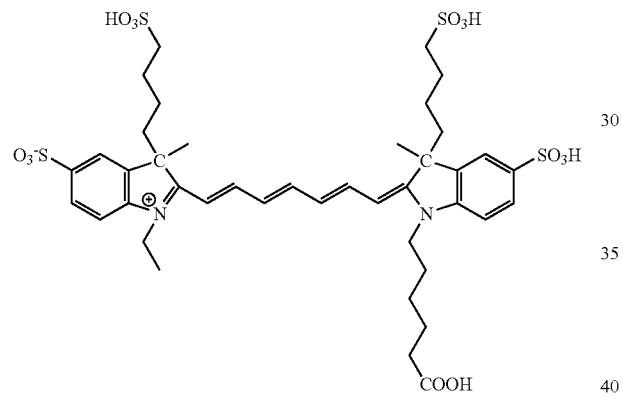

1-Ethyl-2,3-dimethyl-3-(4-sulphobutyl)-3H-indolium-5-sulphonate salt (100 mg) and N-[5-(phenylamino)-2,4-pentadienylidene) aniline mono hydrochloride (60 mg) were heated together in a mixture of acetic acid (5 ml), acetic anhydride (5 ml) and triethylamine (0.5 ml) at 120° C. for 30 mins. To the reaction mixture was then added 1-(5-carboxypentyl)-2,3-dimethyl-3-(4-sulphobutyl)-3H-indolium-5-sulphonate (100 mg) and pyridine (5 ml), the reaction mixture was heated for a further 30 mins at 120° C. On cooling the dark green reaction mixture was poured into an excess of ethyl acetate (250 ml) and the resultant solid filtered off, washed with ethyl acetate and dried. The product was purified by HPLC (Vydac protein & peptide C18 (250 mm×25 mm); flow rate; 10 ml/min; gradient of 5 to 15% B over 30 mins; eluant A=0.1% triethylamine in water and eluant B=0.1% triethylamine in methanol; detection at 650 nm and then changing the gradient of 2 to 25% B over 30 mins; eluant A=0.1% TFA in water and eluant B=0.1% TFA in acetonitrile). Fractions containing the desired product were pooled and the solvent removed under reduced pressure. The product was obtained as a dark green solid (7 mg).

LC-MS (ES$^+$): found 927. $MH^+=C_{41}H_{54}N_2O_{14}S_4$ requires 927.

UV/Vis is; λmax 754 nm (PBS buffer).

4. 2-{(1E,3E,5E,7E)-7-[5-(Carboxymethyl)-3-methyl-1,3-bis(4-sulphobutyl))-1,3-dihydro-2H-indol-2-ylidene]hepta-1,3,5-trienyl}-1-ethyl-3-methyl-3-(4 sulphobutyl)-3H-indolium-5-sulphonate (Compound 4)

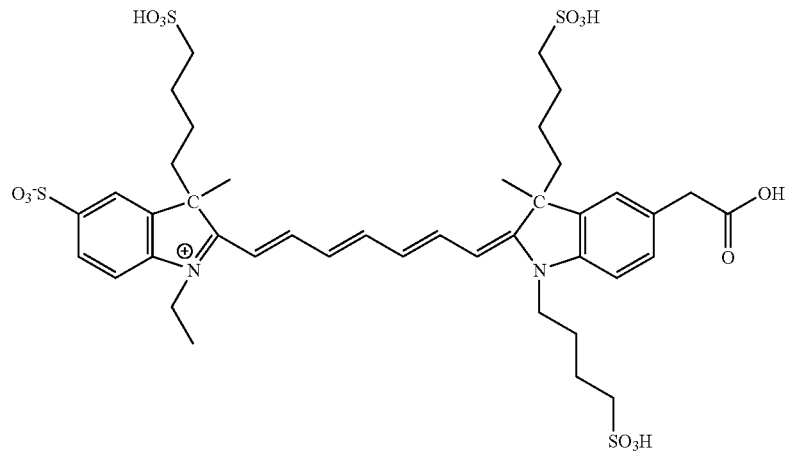

4.1 [2,3-Dimethyl-3-(4-sulphobutyl)-3H-indol-5-yl]acetic acid

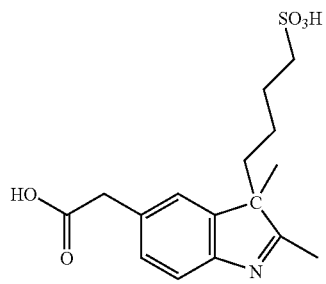

4-(Carboxymethyl)phenylhydrazine hydrochloride (5 g, 0.025 mol) and 5-methyl-6-oxoheptane-1-sulfonic acid (5 g, 0.024 mol) were heated together in acetic acid at 140° C. for 5 hrs and then cooled to RT. The reaction mixture was filtered to remove any particulates and the acetic acid then removed under reduced pressure to leave a dark brown residue. The residue was dissolved in water and re-filtered to remove a dark brown impurity. The product dissolved in water was purified by HPLC (Prep AKTA; Phenomenex C18 column (250 mm×50 mm); flow rate 100 ml/min; gradient of 0 to 100% B over 30 mins; eluant A=0.1% TFA in water and eluant B=0.1% TFA in acetonitrile; detection at 220 nm). The fractions containing the desired product were pooled and the solvent removed under reduced pressure, the residue was then freeze dried. The product was obtained as a rust brown solid (4.14 g).

LC-MS (ES+) found 340. $MH^+=C_{16}H_{22}NO_5S$ requires 340.

$^1$H NMR (D$_2$O) δ 0.90 (m, 2H), 1.68 (m, 5H), 2.23 (m, 2H), 2.75 (m, 4H), 3.88 (s, 2H), 7.49, 7.64 (dd, 2H), 7.64 (s, 1H).

4.2 5-(Carboxymethyl)-2,3-dimethyl-1,3-bis(4-sulphobutyl)-3H-indolium

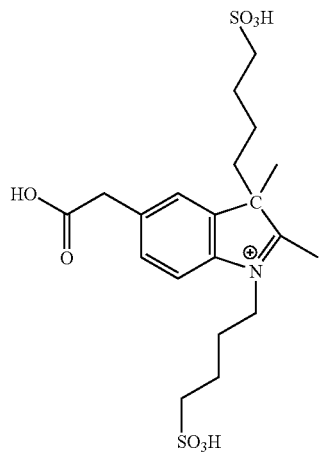

2,3-Dimethyl-3-(4-sulphobutyl)-3H-indol-5-yl]acetic acid (0.89 g, 2.63 mmol) and sodium acetate-tri-hydrate (0.46 g) were dissolved in methanol (30 ml) and stirred for 10 mins at RT. The solvents were removed under reduced pressure, the residue redissolved in methanol (30 ml) and again solvent removed under reduced pressure to give a pale brown residue. To this was added tetramethylene sulfone (5 ml) and 1,4-butane sultone (0.67 ml, 6.56 mmol). The reaction mixture was heated under nitrogen at 150° C. for 6 hrs; a dark purple residue separates around the side of the flask. This was cooled to room temperature and supernatant poured off, and the residue triturated with ethyl acetate to give a purple solid. Product filtered off and washed with ethyl acetate (material very hygroscopic). The product was dissolved in water containing 2% TFA and left to stand for 12 hrs. The product was purified by HPLC (Vydac protein & peptide C18 column (250 mm×25 mm); flow rate; 10 ml/min; gradient of 0 to 25% B over 30 mins; eluant A=0.1% triethylamine in water and eluant B=0.1% triethylamine in methanol; detection at 220 nm). Fractions containing the desired product were pooled and the solvent removed under reduced pressure. The product was obtained as a pale purple residue (0.64 g).

LC-MS (ES+): found 476. $M^+=C_{20}H_{30}NO_8S_2$ requires 476.

$^1$H NMR (D$_2$O) δ 0.85 (m, 2H), 1.31 (t, 24H), 1.58 (s, 3H), 1.76 (m, 2H), 1.95 (q, 2H), 2.12 (m, 2H), 2.26 (m, 2H), 2.73 (t, 2H), 2.96, (t, 2H), 3.20 (q, 18H), 3.78 (s, 2H), 4.55 (t, 2H), 7.75, 7.78 (dd, 2H), 7.63 (s, 1H).

4.3 2-{(1E,3E,5E,7E)-7-[5-(Carboxymethyl)-3-methyl-1,3-bis(4-sulphobutyl)-1,3-dihydro-2H-indol-2-ylidene]hepta-1,3,5-trienyl}-1-ethyl-3-methyl-3-(4-sulphobutyl)-3H-indolium-5-sulphonate 5-(Carboxymethyl)-2,3-dimethyl-1,3-bis(4-sulphobutyl)-3H-indolium (640 mg) and N-[5-(phenylamino)-2,4-pentadienylidene] aniline monohydrochloride (125 mg) were heated together in a mixture of acetic acid (5 ml), acetic anhydride (5 ml) and triethylamine (0.5 ml) at 120° C. for 40 mins. To the reaction mixture was then added 1-ethyl-2,3-dimethyl-3-(4-sulfobutyl)-3H-indolium-5-sulfonate salt (825 mg (30% purity) and pyridine (5 ml), the reaction mixture was heated for a further 40 mins at 120° C. On cooling the dark green reaction mixture was poured into an excess of ethyl acetate (500 ml) and the resultant solid filtered off, washed with ethyl acetate and dried. The product (950 mg) was purified as required using HPLC (Vydac protein & peptide C18 (250 mm×25 mm); flow rate; 10 ml/min; gradient of 15 to 30% B over 30 mins; eluant A=0.1% TFA in water and eluant B=0.1% TFA in acetonitrile). Fractions containing the desired product were pooled and the solvent removed under reduced pressure. The product was obtained as a dark green solid (11.7 mg from 150 mg crude material).

LC-MS (ES+): found 927. $MH^+=C_{41}H_{54}N_2O_{14}S_4$ requires 927.

UV/Vis is; λmax 756 nm (PBS buffer).

5. 1-Benzyl-2-{(1E,3E,5E)-5-[1-(5-carboxyentyl)-3-methyl-5-sulpho-3-(4-sulphobutyl)-1,3-dihydro-2H-indol-2-ylidene]penta-1,3-dienyl}-3-methyl-3-(4-sulphobutyl)-3H-indolium-5-sulphonate (Compound 5)

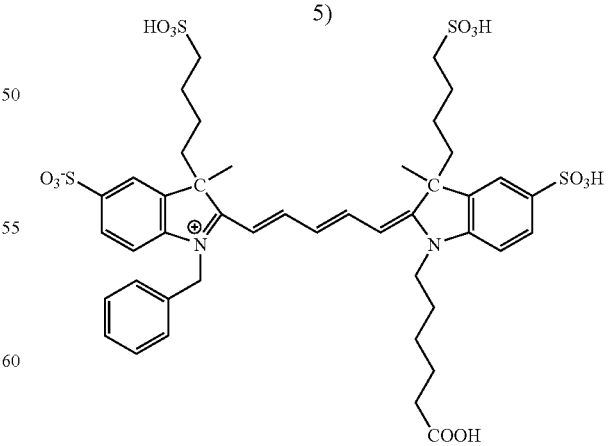

5.1 1-Benzyl-2,3-dimethyl-3-(4-sulphobutyl)-3H-indolium-5-sulphonate salt

Disodium 2,3-dimethyl-3-(4-sulphonatobutyl)-3H-indole-5-sulphonate (5 g, 13.9 mmol) and sodium acetate (3.11 g) were stirred with methanol (100 ml) for 1 hour. Solvent removed by rotary evaporation and a further portion of methanol (100 ml) added. This was removed by rotary evaporation to yield an orange sticky solid. To this was added sulfolan (25 ml) and benzyl bromide (9.51 g, 55.6 mmol, 4 eq). The mixture was stirred overnight at 110° C. under a blanket of nitrogen. The cooled red solution was poured into stirring ethyl acetate (1 l) and the precipitate filtered off. The precipitate washed with copious ethyl acetate and diethyl ether and then dried under vacuum. A sample was dissolved in water and analysed by reverse Phase TLC using acetonitrile modified with 0.1% TFA: water modified with 0.1% TFA (30:70). Separation yielded the product ($R_f$ 0.6) and starting material ($R_f$ 0.95). The product spot turned red on standing indicating quaternisation had taken place. Yield: 8 g.

5.2 1-Benzyl-2-{(1E,3E,5E)-5-[1-(5-carboxypentyl)-3-methyl-5-sulpho-3-(4-sulphobutyl)-1,3-dihydro-2H-indol-2-ylidene]penta-1,3-dienyl}-3-methyl-3-(4 sulphobutyl)-3H-indolium-5-sulphonate 1-Benzyl-2,3-dimethyl-3-(4-sulphobutyl)-3H-indolium-5-sulphonate salt (2 g), 1-(5-carboxypentyl)-2,3-dimethyl-3-(4-sulphobutyl)-3H-indolium-5-sulphonate (2 g) and malonaldehyde bis-phenylimine (2 g) were dissolved in acetic acid: pyridine: acetic anhydride (4.5:4.5:1) (100 ml). The mixture was heated at 90° C. for 2 hours. The mixture went blue/green immediately. A small sample was diluted in water for UV measurement. UV/Vis is absorption spectroscopy observed a peak at 650 nm showing formation of Cy5. The reaction mixture was stored overnight at +2° C. The mixture was rotary evaporated to yield an oil. This was pumped under vacuum for several hours to ensure dryness. The sticky solid washed with acetonitrile (4×500 ml) to yield a dry powder that was filtered and washed with more acetonitrile. The solid was dried under vacuum. Yield: 3.05 g.

The dye was dissolved in water (7.5 ml), filtered and purified by HPLC (Dynamax $C_{18}$ 42 mm×25 cm) using water (0.1% TFA) modified with a 20 to 30% acetonitrile (0.1% TFA) gradient over 60 minutes. The flow rate was 20 ml/min. Fractions containing desired product were combined and rotary evaporated to a small volume, transferred to a small bottle and freeze-dried o/n. UV/Vis is detection was at 650 nm. Yield: 132 mg. The partially purified material was then dissolved in water (7.5 ml), filtered and purified by HPLC (Dynamax $C_{18}$ 42 mm×25 cm) using Water (0.1% TFA) modified with 20-30% acetonitrile (0.1% TFA) over 60 minutes. The flow rate was 20 ml/min. Final yield 103 mg.

Analysis of the probe showed an extinction coefficient: 156175 $M^{-1}$ $cm^{-1}$, $\lambda_{max}$ 652 nm Fluorescence emission$_{max}$: 670 nm (exc. 652 nm) and a fluorescence purity: 99.6%.

5.3 Preparation of Compound 5, NHS Ester

1-Benzyl-2-{(1E,3E,5E)-5-[1-(5-carboxypentyl)-3-methyl-5-sulpho-3-(4-sulphobutyl)-1,3-dihydro-2H-indol-2-ylidene]penta-1,3-dienyl}-3-methyl-3-(4-sulphobutyl)-3H-indolium-5-sulphonate (5 mg) was dissolved in DMSO (2.2 ml) and DIPEA (80 µl) containing HSPyU (10 mg). The mixture was rolled for 2 hours. 400 µl aliquots were dispensed into Sarstedt tubes containing 1 ml of dry ethyl acetate. Tubes were centrifuged for 15 minutes and the ethyl acetate decanted off. HPLC analysis separated the product from any trace of starting materials, the acid had a retention time of 22.5 minutes and the ester 31.38 minutes with a purity of 96.01% NHS ester

6. Labelling Study with Cy5 Dyes. Comparison of Compound 2 with Cy5™ (Compound 6)

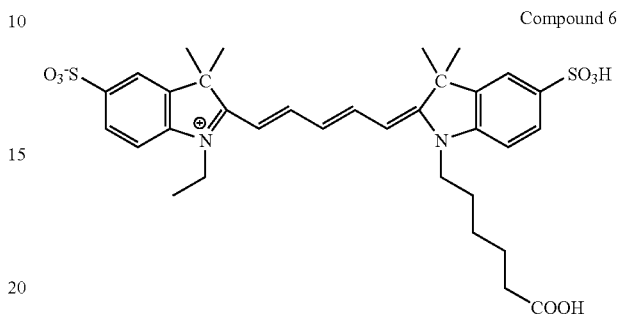

Compound 6

6.1 Conversion of Carboxy Dyes to NHS Esters

In separate Sarstedt tubes, Compounds 2 and 6 (2.5 mg each) and O—(N-succinimidyl)-N,N,N',N'-tetramethyluronium tetrafluoroborate (TSTU, 10 mg) were mixed with anhydrous DMF (100 µl). To both of the resulting solutions was then added N,N-diisopropylethylamine (10 µl). The tubes were capped, vortexed and left to stand for 1 hr. At the end of this time the reaction mixtures were diluted with ethyl acetate, vortexed and then centrifuged to collect the NHS esters. The supernatant liquors were decanted; the pellets were washed with fresh ethyl acetate and dried under vacuum. Reaction was confirmed by mass spectrum (MALDI-TOF).

Compound 2: $C_{45}H_{59}N_3O_{19}S_5$ requires $M^+$=1105; found $M^+$=1104.

Compound 6 (Cy5): $C_{37}H_{43}N_3O_{10}S_2$ requires $M^+$=753; found $M^+$=752.

6.2 Labelling of Sheep γ-Globulin with the NHS Derivatives of Cy5 Dyes (Compounds 2 and 6)

Sheep IgG, was dissolved in sodium carbonate buffer (0.1M, pH 9.2) at 1 mg/ml; the dye NHS esters were dissolved in anhydrous DMSO at ~10 mg/ml (250 µl). In order to obtain a range of dye/protein ratios, a series of labelling experiments was carried out. Each reaction used 500 µl of antibody solution, combined with varying amounts of dye NHS ester solution, ranging from 0.1-32.0 µl. The labelling reactions were rolled in the dark at ambient temperature for 45 minutes. Free dye was removed from the conjugates by purification by size exclusion chromatography using Sephadex as the stationary phase and phosphate buffered saline (PBS) of pH 7.4 as the eluant. For reactions using compound 2, the purified antibody fractions were additionally subjected to dialysis to ensure complete removal of unbound dye.

6.3 Characterisation of Conjugates by UV/Vis is Spectra

Absorbance spectra were first measured on the neat conjugate solutions: in cases where the dye absorbance exceeded the linear range of the instrument (~1.5 AU), a more dilute sample was made up using PBS and the readings scaled appropriately. Absorbance values were recorded at the dye absorption peak (~650 nm) and at the antibody absorbance (280 nm).

Dye/protein ratios were calculated using the standard formula:

$$D/P = \frac{A_{max} \cdot \varepsilon_{AB}}{(A_{280} - x \cdot A_{max}) \cdot \varepsilon_D}$$

$\lambda_{max}$=the absorbance at the dye peak wavelength (~650 nm),
$\varepsilon_D$=the extinction coefficient of the dye at the dye peak wavelength (~250,000 dm$^3$ mol$^{-1}$ cm$^{-1}$),
$A_{280}$=the absorbance at 280 nm (the absorbance peak of the antibody),
x=the extinction coefficient of the dye at 280 nm, relative to the dye peak extinction coefficient (determined by mathematical analysis of the results and by spectral analysis of pure dyes, =0.05),
$\varepsilon_{AB}$=the extinction coefficient of the antibody at 280 nm (determined by experiment to be 170,000 dm$^3$ mol$^{-1}$ cm$^{-1}$).

Figure 1B:
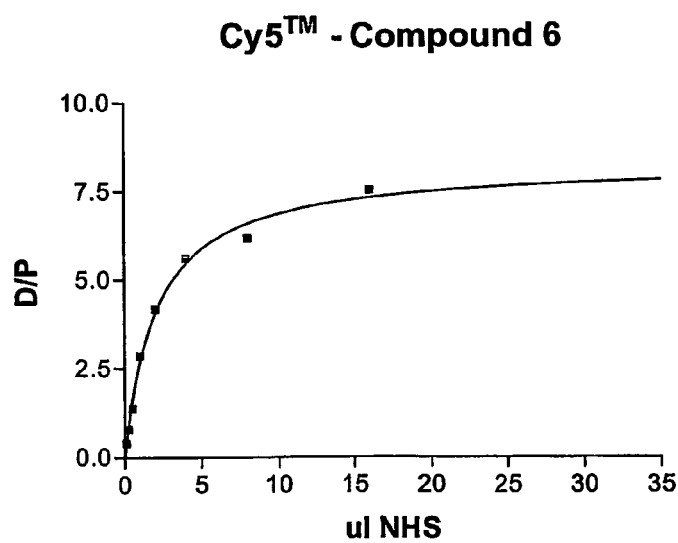

The results were processed for both dyes and displayed as plots of (dye/protein ratio) versus (amount of applied dye-NHS). The plots are shown in FIG. 1 (1A and 1B). It can be seen that the labelling efficiencies of the two dyes are comparable.

Figure 2:
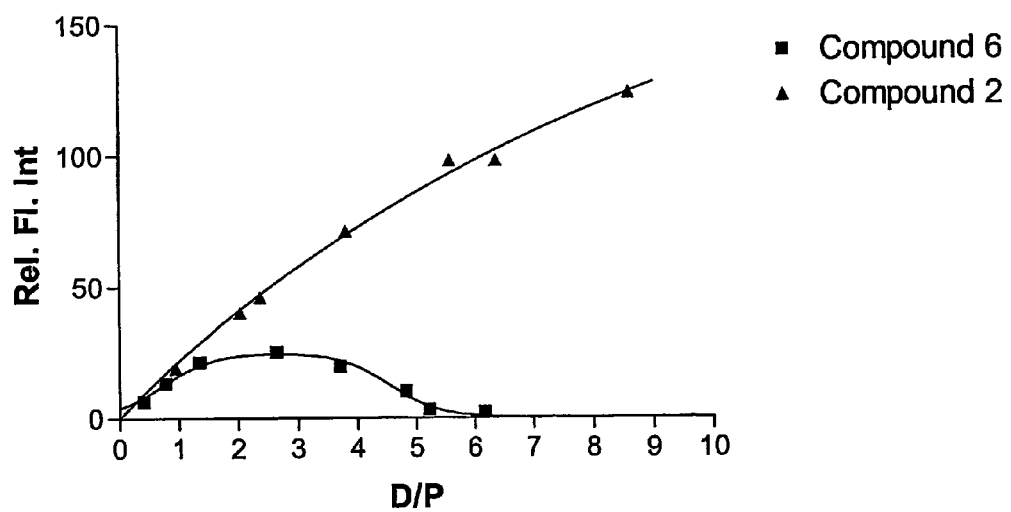
FIG. 2 is plot of relative fluorescence intensity versus dye/protein ratio at constant antibody concentration for pentamethine cyanine dyes.

The conjugate solutions were diluted with PBS (200 μl conjugate into 20 ml) and the fluorescence reading determined on a Perkin Elmer LS-55 instrument. Excitation was at the dye peak absorbance wavelength; emission at 680 nm was recorded. Initial fluorescence readings were processed to take account of the actual concentration of antibody in each sample, as determined from the absorbance data. The readings for both sets of conjugates were thus scaled to a constant concentration of antibody; relative fluorescence was then plotted versus dye/protein ratio: FIG. 2.

The results indicate that conjugates of Compound 2 with the protein IgG are brighter at higher loadings of dye than the standard Cy5 (Compound 6-IgG conjugates). The reason for this difference in performance is attributed to a marked decrease in the tendency of the dyes to associate via aggregation, when bound in close proximity to each other. This reduction in aggregation can be explained by two factors. Firstly, the increased negative charge on each dye label causes an increase in charge-charge repulsion, which acts to counter the normal attraction of the planar aromatic systems due to π-π stacking interactions. Secondly, the greater steric bulk of the new dyes acts to block close approach of the dye molecules, further preventing the stacking interaction.

Figure 3A:
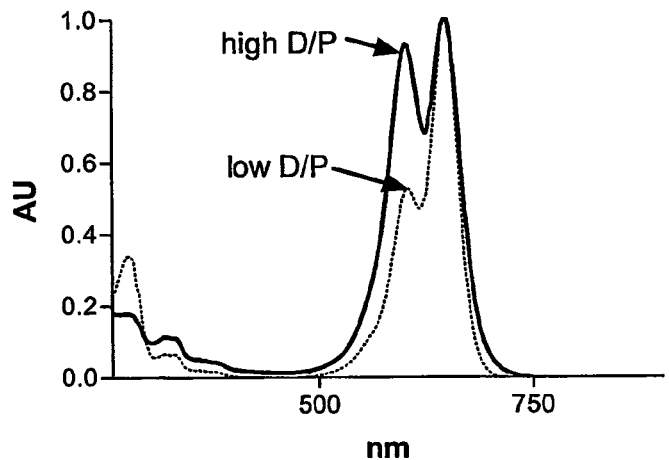
FIG. 3 shows the absorption spectra of IgG Conjugates of Compound 5 and Compound 2 at low- and high-dye/protein ratios.
Figure 3B:
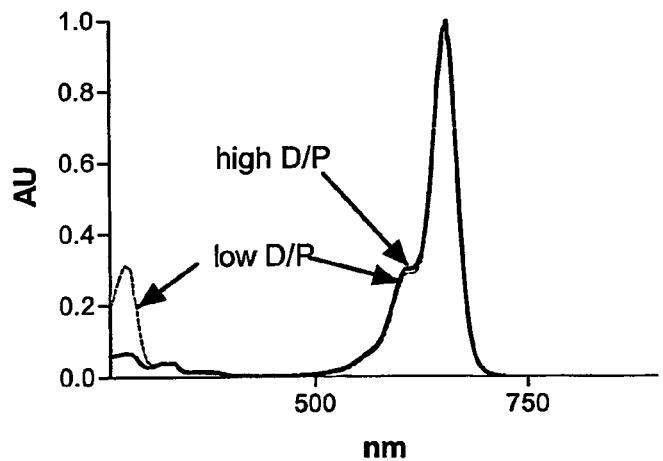

The reduction in dye aggregation can be observed via the absorbance spectra of the conjugates. Aggregation of cyanine dyes in solution is known to lead to an increase in absorbance of the high-energy shoulder on the main absorption peak. This effect is clearly visible in the absorption spectra of the Cy5™ conjugates, becoming more pronounced as the dye/protein ratio increases: see FIG. 3A. In contrast, the equivalent absorption spectra for conjugates of Compound 2 do not show this effect; the dye absorption band for the conjugates is essentially independent of dye/protein ratio and the spectra are superimposable: see FIG. 3B.

7. Labelling Study with Cy7 Dyes: Comparison of Compounds 3 and 4 with Cy7 (Compound 7)

The performance of the heptamethine cyanine dye examples of the invention were compared to the commercially available Cy7 derivative, (Compound 7).

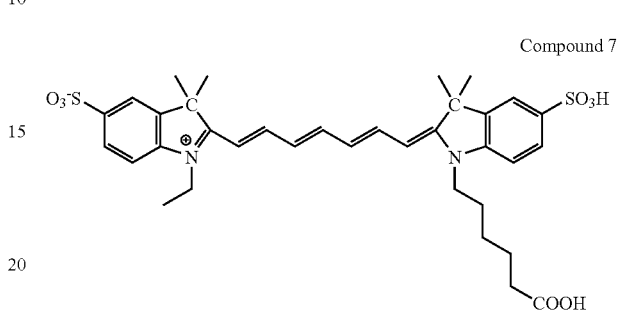

Compound 7

7.1 Conversion of Carboxy Dyes to NHS Esters

Compounds 3 and 4 were converted to their NHS ester derivatives using the method of Example 6.1.
Compound 3: $C_{45}H_{58}N_3O_{16}S_4$ requires M$^+$=1024; found M$^+$=1024.
Compound 4: $C_{45}H_{58}N_3O_{16}S_4$ requires M$^+$=1024; found M$^+$=1024.

7.2 Labelling of Sheep γ-Globulin with the NHS Derivatives of Heptamethine Cyanine Dyes: Compounds 3.4 and 7

Sheep IgG, was dissolved in sodium carbonate buffer (0.1M, pH 9.2) at 1 mg/ml; the dye NHS esters were dissolved in anhydrous DMSO at ~10 mg/ml (250 μl). In order to obtain a range of dye/protein ratios, a series of labelling experiments was carried out. Each reaction used 500 μl of antibody solution, combined with varying amounts of dye NHS ester solution, ranging from 0.5-16 μl. The labelling reactions were rolled in the dark at ambient temperature for 45 minutes. Free dye was removed from the conjugates by purification by size exclusion chromatography using Sephadex as the stationary phase and phosphate buffered saline (PBS) of pH 7.4 as the eluant.

7.3 Characterization of Conjugates by UV/Vis is Spectra

Absorbance spectra were first measured on the neat conjugate solutions; in cases where the dye absorbance exceeded the linear range of the instrument (~1.5 AU), a more dilute sample was made up using PBS and the readings scaled appropriately. Absorbance values were recorded at the dye absorption peak (~750 nm) and at the antibody absorbance (280 nm).

Dye/protein ratios were calculated using the standard formula given in Example 6; $\varepsilon_D$ was taken as 250,000 dm$^3$ mol$^{-1}$ cm$^{-1}$ and x as 0.04.

Figure 4A:
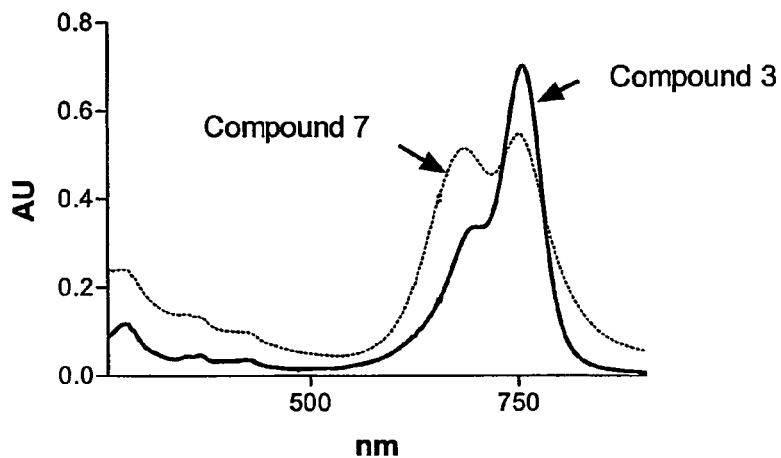
FIG. 4 shows the absorption spectra of IgG conjugates of Compound 6 compared with Compounds 3 and 4 at high-dye/protein ratios.

As seen in FIG. 4, UV/Vis absorbance of the conjugates in PBS shows Cy7 (Compound 7) within the Cy7-IgG constructs to be highly aggregated at higher dye/protein ratios as indicated by the magnitude of the blue-shifted shoulder: FIG.

Figure 4B:
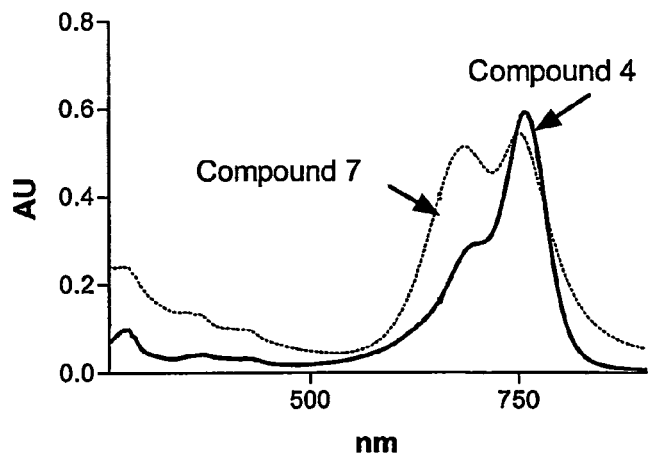

4A. IgG conjugates of Compounds 3 and 4 are demonstrated not to exhibit this aggregation property: FIG. 4B.

7.4 Characterization of Conjugates by Fluorescence

Figure 5:
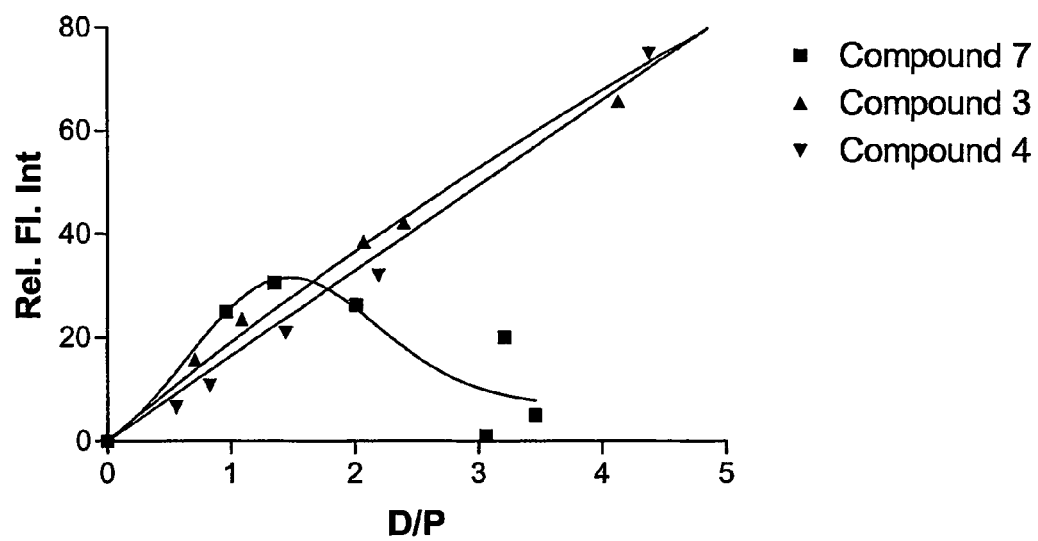
FIG. 5 is a plot showing relative fluorescence intensity versus dye/protein ratio for heptamethine cyanine dyes.

UV/Vis is solutions were diluted further with PBS buffer in order to measure the relative fluorescence of the different heptamethine cyanine dye-labelled conjugates. Relative fluorescence was measured as described in Example 6.3 and then plotted versus dye/protein ratio: FIG. 5. The results indicate that the IgG conjugates with Compounds 3 and 4 are brighter at higher loadings of dye than the standard Cy7 6-IgG conjugates.

8. Labelling of Aminoallyl 2'-deoxyuridine-5'-triphosphate with Compound 2

8.1 Aminoallyl-dUTP was dissolved in carbonate buffer (10 ml, pH 9.2). To this was added N-trifluoroacetyl aminohexanoyl N-hydroxysuccinimide (2 equivalents) in acetonitrile. This was stirred at room temperature for 4.5 hours. Analytical HPLC showed the completion of this reaction. Ammonium hydroxide (0.88 S.G., 10 ml) was then added and the mixture stirred overnight to yield aminohexanoyl-aminoallyl-dUTP. This product was purified by reverse phase HPLC.

8.2 Aminohexanoyl-aminoallyl-dUTP (1 mg) in DMSO (500 µl) and diisopropylethylamine (40 µl) were stirred for 15 minutes under nitrogen in an oven dried 25 ml round bottomed flask. Compound 2 NHS ester (1 mg) was dissolved in DMSO (300 µl) and added in one portion to the mixture. The vial was rinsed with DMSO (200 µl) which was also added. DMAP (~1 mg) was added and the mixture stirred for 18 hours in the dark under nitrogen. A sample (25 µl in 500 µl buffer) was analysed using analytical HPLC (Phenomenex Jupiter $C_{18}$ 10µ 25×0.46 cm) in phosphate buffer 0.05M pH 5.6 modified with a 5 to 30% acetonitrile gradient over 30 minutes and constant flow rate of 1 ml/minute. Sample detection was made using absorbance at 254 nm and 650 nm. The chromatogram shows consumption of ester and amine to give a new product with a $R_T$ of 15.5 minutes. The product was diluted with water (1 ml) and purified by ion-exchange chromatography (HiTrap Q HP 5 ml) in 0.1M triethyl ammonium bicarbonate buffer modified with 20-75% 1M triethyl ammonium carbonate buffer over 60 minutes. The flow rate was 1 ml/min and detection was at 650 nm and 254 nm. Fractions corresponding to the major peak were combined and rotary evaporated with heat, dissolved in water, and freeze-dried.

9. Labelling of cDNA Using Compounds 2 and 5

9.1 cDNA Probe Labelling cDNA was labelled using Compounds 2 and 5 by means of a post-labelling technique in which the reactive NHS ester derivatives of the dyes were coupled to cDNA to generate microarray probes as described below.

Purified human skeletal muscle messenger RNA (1 µg) was converted into cDNA using oligo-dT and random primers in the presence of aminoallyl-deoxyUTP, deoxynucleotides, reverse transcriptase and reaction buffer for 1 hour at 42° C. in 20 µl reactions following standard protocol outlined in the CyScribe Post Labelling Kit (GE Healthcare). Unincorporated nucleotides and buffers were removed from synthesized cDNA by binding cDNA on a glass-bead matrix. The aminoallyl-cDNA was eluted in water.

The eluted cDNA was dried down and resuspended in aliquots of 0.1M sodium bicarbonate buffer, pH 8.5 (40 µl) and separate aliquots mixed with reactive NHS esters of Compounds 2 and 5. Equal amounts of cDNA were used with 100-500 µg of Compounds 2 and 5 as their reactive NHS esters. The coupling reaction was carried out in the dark for 1 hr 30 minutes, followed by purification of labelled cDNA from un-reacted ester using a glass bead matrix. For comparison purposes, an aliquot of the cDNA was also labelled with Compound 6 (Cy5 NHS ester). The cDNA labelled probes were purified and the yields determined as described below.

i) Calculation of Yield of Labelled cDNA $\text{Yield}_{cDNA}=\text{DNA AbS}_{260\ nm} \times 37$ µg/ml×Total Probe Volume (ml)

ii) Dye Incorporation:

$$\text{Moles of Dye Incorporated} = \frac{\text{Abs}_{max}}{\varepsilon} \times \text{Total Probe Volume}$$

$\text{Abs}_{max}$=the absorbance at the dye peak wavelength (650 nm).
$\varepsilon$=the extinction coefficient of the dye at the dye peak wavelength (250,000 $\text{mol}^{-1}\ \text{cm}^{-1}$).

iii) Nucleotide/Dye Ratio $$N/D\ \text{Ratio} = \frac{\text{Yield of } cDNA\ (ng) \times 1000}{pmoles\ \text{of probe} \times 324.5}$$

The above calculation assumes an average probe size of 1000 bases and an average molecular weight of dNMP in cDNA to be 324.5. The results from labelling reactions are shown in Table 5.

TABLE 5

| Compound No. | Amount | $OD_{260}$ | $OD_{650}$ | cDNA (ng) | Probe (pmoles) | N/D Ratio |
|---|---|---|---|---|---|---|
| 2 | 100 µg | 0.395 | 0.170 | 1169 | 54 | 66 |
| 2 | 150 µg | 0.382 | 0.280 | 1131 | 90 | 39 |
| 2 | 200 µg | 0.380 | 0.400 | 1125 | 128 | 27 |
| 5 | 100 µg | 0.394 | 0.420 | 1166 | 134 | 27 |
| 5 | 150 µg | 0.384 | 0.520 | 1137 | 166 | 21 |
| 5 | 200 µg | 0.383 | 0.600 | 1134 | 192 | 18 |
| 5 | 200 µg | 0.352 | 0.564 | 1042 | 180 | 18 |
| 6 | 20 µg | 0.320 | 0.260 | 947 | 83 | 35 |
| 6 | 20 µg | 0.287 | 0.260 | 850 | 83 | 31 |

Figure 6:
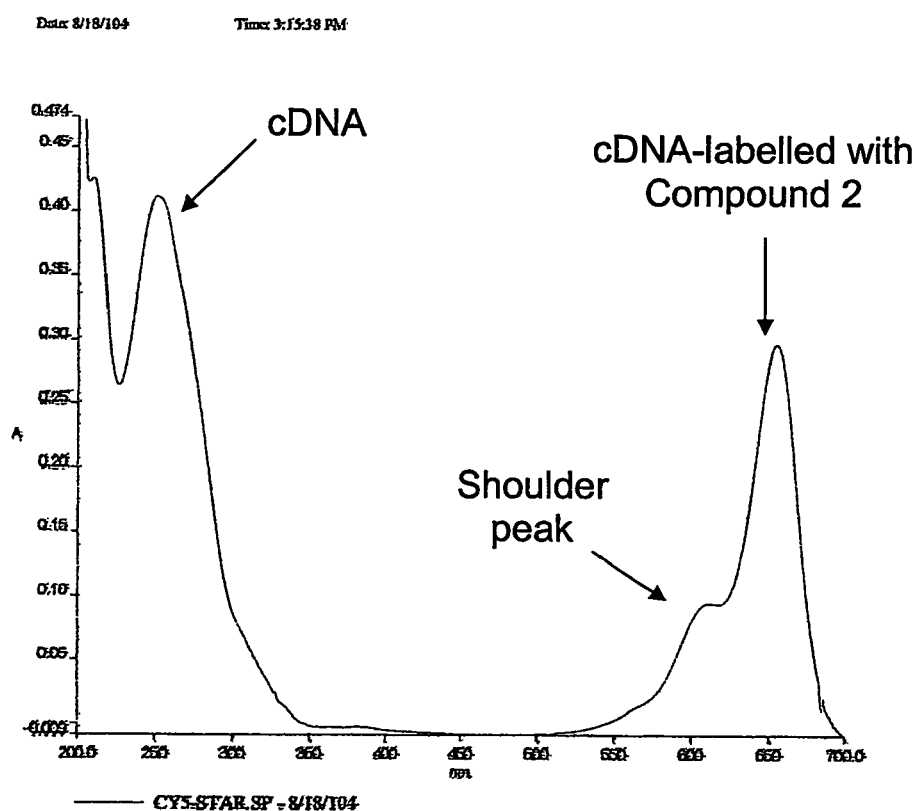
FIG. 6 is a spectral scan (200-700 nm) of cDNA labelled with Compound 2.
Figure 7:
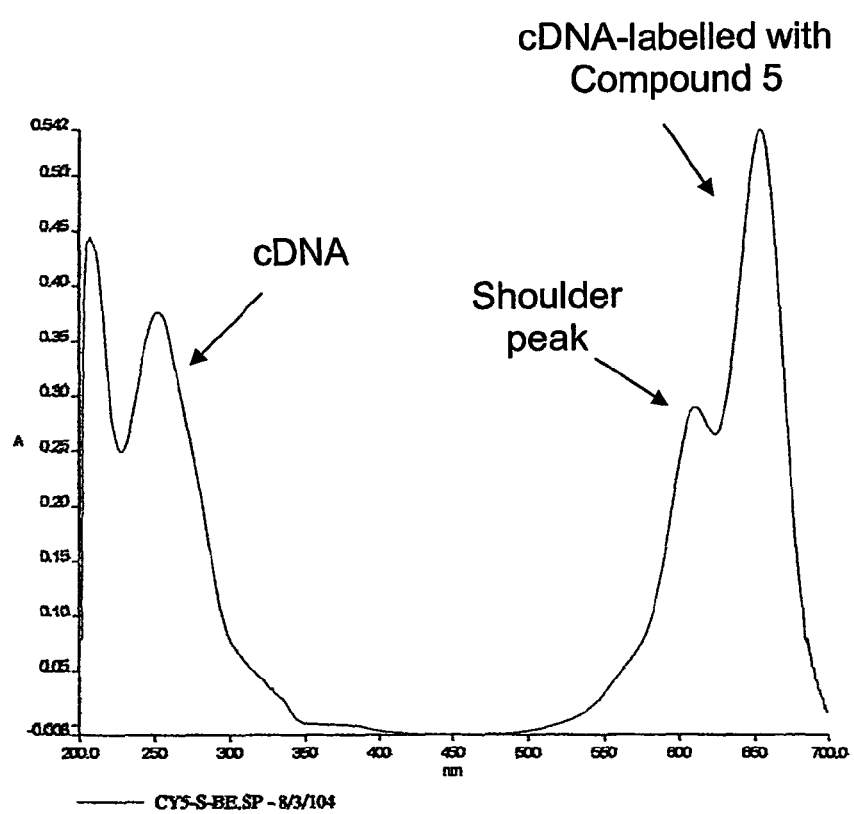
FIG. 7 is a spectral scan (200-700 nm) of cDNA labelled with Compound 5.
Figure 8:
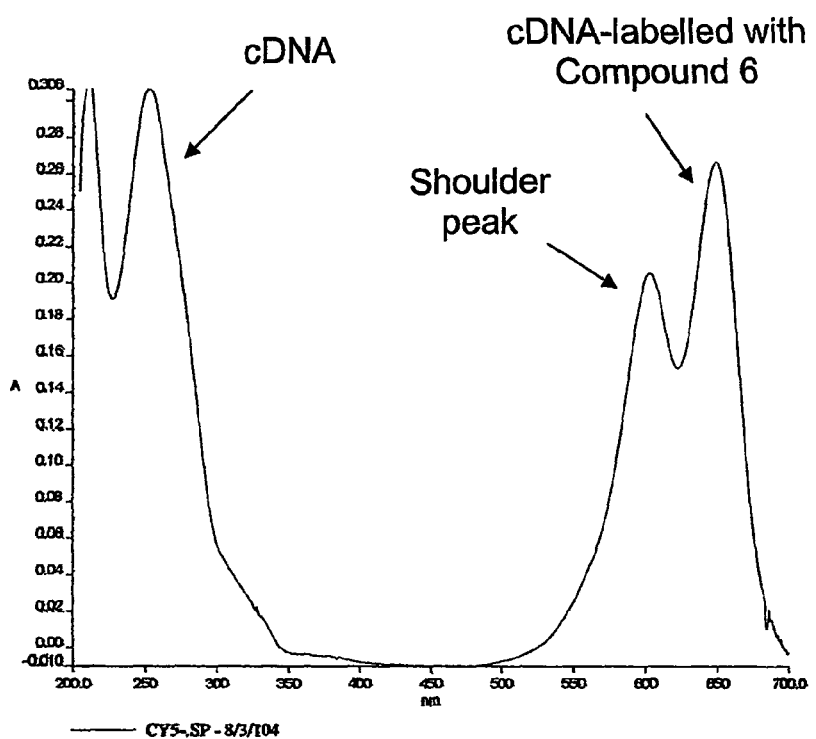
FIG. 8 is a spectral scan (200-700 nm) of cDNA labelled with Compound 6.

Whilst the labelling efficiency of Compound 6 was higher than either of Compounds 2 and 5, this was overcome by adding larger quantities of the latter reactive dyes to the labelling mix. Compound 5 gave higher coupling efficiencies than Compound 2, probably due to improved aqueous stability of Compound 5. Furthermore, the presence of multiple sulphonate groups in the structures of the dyes according to the present invention appears to diminish probe aggregation as indicated by a reduction in the shoulder absorbance peak at 605 nm adjacent to the dye fluorescence maxima at 650 nm (see FIGS. 6 and 7). This is in contrast to the Compound 6-labelled cDNA probe which shows a large shoulder peak at 605 nm adjacent to the maxima at 650 nm (FIG. 8).

10. Dye Photostability

Figure 9:
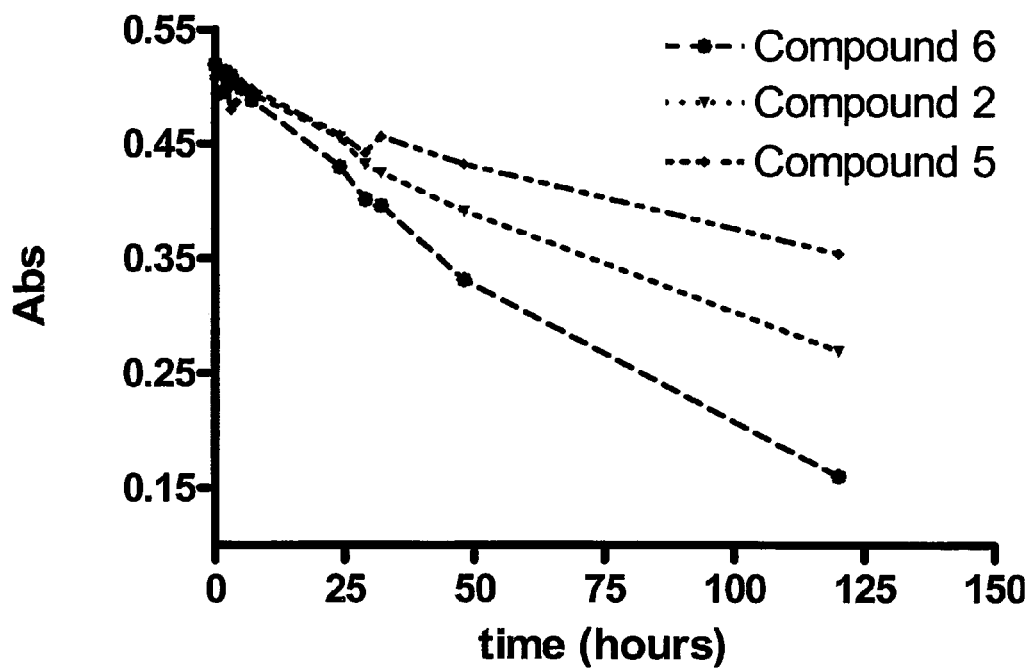
FIG. 9 is a plot showing UV absorbance measured at intervals over 120 hours for Compounds 2, 5 and 6.

Compounds 2, 5 and 6 were diluted to ~0.5 AU, total volume 10 ml in scintillation vials. The vials were placed on a light box in a temperature controlled room at 20° C. The UV absorbance was measured at intervals over 120 hours. The results are shown in FIG. 9, and indicate that photostability of cyanine dyes containing multiple sulphonate groups attached to the chromophore structure is enhanced compared with dyes containing fewer such groups.

Duplicate samples were also stored under the same conditions, but in the dark. No change in UV absorbance was observed in these samples.

What is claimed is:

1. A compound of formula (I):

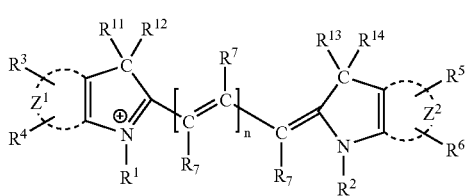

(I)

wherein:

$Z^1$ and $Z^2$ independently represent the carbon atoms necessary to complete a one ring, or two-fused ring aromatic system;

$R^1$ and $R^2$ are independently chosen from the group -E-F, $C_1$-$C_6$ alkyl, benzyl either unsubstituted or substituted with sulphonic acid, and the group —$(CH_2)_k$—W, where W is sulphonic acid or phosphonic acid and k is an integer from 1 to 10;

$R^3$ and $R^4$ are attached to the $Z^1$ ring structure and groups $R^5$ and $R^6$ are attached to the $Z^2$ ring structure, and n=1, 2 or 3;

$R^3$, $R^4$, $R^5$ and $R^6$ are independently selected from the group -E-F, hydrogen and sulphonic acid;

each $R^7$ is independently the group -E-F, hydrogen or two of $R^7$ together with the group,

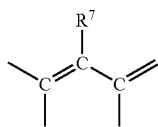

form a hydrocarbon ring system having 5 or 6 atoms;

each $R^{11}$, $R^{12}$, $R^{13}$ and $R^{14}$ is independently a group —$(CH_2)_k$—W as defined above, or $C_1$-$C_6$ alkyl;

E is a single bond or a spacer group having a chain from 1-20 linked atoms selected from the group consisting of carbon, nitrogen and oxygen atoms and F is a target bonding group;

wherein F is either:

(i) a reactive group selected from carboxyl, succinimidyl ester, sulpho-succinimidyl ester, isothiocyanate, maleimide, haloacetamide, acid halide, hydrazide, vinylsulphone, dichlorotriazine and phosphoramidite; or (ii) a functional group selected from hydroxy, amino, sulphydryl, carbonyl (including aldehyde and ketone) and thiophosphate; or (iii) an affinity tag;

with the provisos that:

(a) one of groups $R^1$, $R^2$, $R^3$, $R^4$, $R^5$, $R^6$ and $R^7$ is the group -E-F;

(b) one or more of $R^{11}$, $R^{12}$, $R^{13}$ and $R^{14}$ is the group —$(CH_2)_k$—W;

(c) the compound of Formula I has from 3 to 5 sulfonic acid groups.

2. A compound according to claim 1 wherein at least two of $R^{11}$, $R^{12}$, $R^{13}$ and $R^{14}$ are independently —$(CH_2)_k$—W.

3. A compound according to claim 1 wherein one of groups $R^{11}$ and $R^{12}$ and one of groups $R^{13}$ and $R^{14}$ is the group —$(CH_2)_k$—W.

4. A compound according to claim 1 wherein W is sulphonic acid.

5. A compound according to claim 1 wherein —$(CH_2)_k$—W is selected from —$(CH_2)_3$—$SO_3H$ and —$(CH_2)_4$—$SO_3H$.

6. A compound according to claim 1 wherein $Z^1$ and $Z^2$ are selected from phenyl and naphthyl moieties.

7. A compound according to claim 1 wherein said target bonding group F comprises an affinity tag.

8. A compound according to claim 1 wherein said spacer group E is selected from:

—(CHR')$_p$-Q-(CHR')$_r$— where Q is selected from: —CHR'—, —NR'—, —O—, —CR'=CR'—, —C(O)—NR'— and —C(O)—O—;

R' is hydrogen or $C_1$-$C_4$ alkyl, p is 0-5 and r is 1-5.

9. A compound according to claim 8 wherein Q is selected from: —CHR'—, —C(O)—NH— and

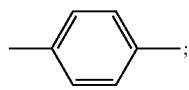

where R' is hereinbefore defined.

10. A compound according to claim 1 wherein said group -E-F comprises a carboxypentyl group.

11. A compound according to claim 1 selected from:

i) 2-{(1E,3E,5E)-5-[1-(5-carboxypentyl)-3-methyl-5-sulpho-3-(4-sulphobutyl)-1,3-dihydro-2H-indol-2-ylidene]penta-1,3-dienyl}-1-ethyl-3-methyl-3-(4-sulphobutyl)-3H-indolium-5-sulphonate;

ii) 2-{(1E,3E,5E)-5-[1-(5-carboxypentyl)-3-methyl-5-sulpho-3-(4-sulphobutyl)-1,3-dihydro-2H-indol-2-ylidene]penta-1,3-dienyl}-3-methyl-1,3-bis(4-sulphobutyl)-3H-indolium-5-sulphonate;

iii) 2-{(1E,3E,5E,7E)-7-[1-(5-carboxypentyl)-3-methyl-5-sulpho-3-(4-sulphobutyl)-1,3-dihydro-2H-indol-2-ylidene]hepta-1,3,5-trienyl}-1-ethyl-3-methyl-3-(4-sulphobutyl)-3H-indolium-5-sulphonate;

iv) 2-{(1E,3E,5E,7E)-7-[5-(carboxymethyl)-3-methyl-1,3-bis(4-sulphobutyl)-1,3-dihydro-2H-indol-2-ylidene]hepta-1,3,5-trienyl}-1-ethyl-3-methyl-3-(4-sulphobutyl)-3H-indolium-5-sulphonate; and v) 1-benzyl-2-{(1E,3E,5E)-5-[1-(5-carboxypentyl)-3-methyl-5-sulpho-3-(4-sulphobutyl)-1,3-dihydro-2H-indol-2-ylidene]penta-1,3-dienyl}-3-methyl-3-(4-sulphobutyl)-3H-indolium-5-sulphonate.

* * * * *